United States Patent [19]

Sohda et al.

[11] Patent Number: 5,741,784

[45] Date of Patent: Apr. 21, 1998

[54] BENZOPYRAN DERIVATIVES AND THEIR USE

[75] Inventors: Takashi Sohda, Takatsuki; Shigehisa Taketomi, Ikeda; Tsuneo Oda, Kyoto, all of Japan

[73] Assignee: Takeda Chemical Industries, Ltd., Osaka, Japan

[21] Appl. No.: 697,862

[22] Filed: Aug. 30, 1996

Related U.S. Application Data

[62] Division of Ser. No. 242,638, May 13, 1994, Pat. No. 5,580,863.

[30] Foreign Application Priority Data

May 18, 1993 [JP] Japan .................................. 5-115950
Mar. 3, 1994 [JP] Japan .................................. 6-33911

[51] Int. Cl.⁶ .................... A61K 31/665; A61K 31/675
[52] U.S. Cl. .................... 514/80; 514/81; 514/82; 514/85; 514/86; 514/89; 514/90; 514/91; 514/92; 514/93; 514/94; 514/95; 514/100
[58] Field of Search ................... 514/100, 95, 94, 514/93, 92, 91, 90, 89, 86, 85, 82, 81, 80; 544/232, 376, 151, 57; 546/21, 22, 23; 548/111, 112, 113, 117, 118; 549/220, 5

[56] References Cited

FOREIGN PATENT DOCUMENTS

| 0 524 023 | 1/1993 | European Pat. Off. . |
|---|---|---|
| 5 6712 07 | 10/1993 | European Pat. Off. . |
| 2 125 245 | 12/1971 | Germany . |
| 53-133635 | 11/1978 | Japan . |
| 63-156720 | 6/1988 | Japan . |
| 63-156721 | 6/1988 | Japan . |
| 63-156722 | 6/1988 | Japan . |
| 63-156723 | 6/1988 | Japan . |
| 92/03451 | 3/1992 | WIPO . |
| 92/06083 | 4/1992 | WIPO . |

OTHER PUBLICATIONS

Martindale, The Extra Pharmacopoeia, 30th Ed., p. 1379–3.

*Primary Examiner*—Nicky Chan
*Attorney, Agent, or Firm*—Foley & Lardner

[57] ABSTRACT

This invention relates to a compound represented by the formula:

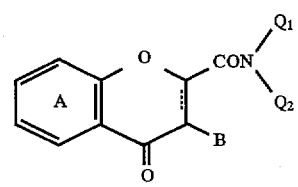

wherein B represents a hydrogen atom or a lower alkyl group; ring A represents a benzene ring which may have one or more substituents; ....... represents a single or double bond; $Q_1$ represents the group represented by the formula,

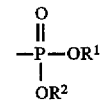

,or a hydrocarbon residue substituted with the group represented by the formula,

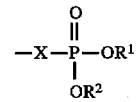

wherein X represents a bond or a spacer having a chain length of 1 to 4 atoms as the linear moiety which may have one or more side chains; $R^1$ and $R^2$, whether identical or not, independently represent a hydrogen atom or a lower alkyl, or may bind together to form a ring; $Q_2$ represents a hydrogen atom, a hydrocarbon residue which may be substituted or a heterocyclic ring residue which may be substituted; or a salt thereof.

8 Claims, No Drawings

BENZOPYRAN DERIVATIVES AND THEIR USE

This application is a division of application Ser. No. 08/242,638, filed May 13, 1994 now U.S. Pat. No. 5,580,863.

FIELD OF THE INVENTION

The present invention relates to a benzopyran derivative which promotes osteogenesis, a method of production thereof and use thereof.

BACKGROUND OF THE INVENTION

Osteoporosis is a pathologic state or disease involving some symptom or risk due to quantitative reduction in bone exceeding a certain degree. Major symptoms are spinal kyphosis, and fractures of dorsolumbar bones, vertebral centra, femoral necks, distal end of radius, ribs, proximal end of humerus, and others. In healthy bone tissue, bone destruction occurs constantly, with a good balance between bone formation and resorption; osteoblasts and osteoclasts play key roles in osteogenesis and bone resorption, respectively. Bone resorption surpassing osteogenesis, upon deterioration of the bone destruction balance therebetween, results in a quantitative reduction in bone. Traditionally, bone resorption inhibitors such as estrogens, calcitonin and bisphosphonates have been mainly used to treat osteoporosis. However, these bone resorption inhibitors fail to have a satisfactory effect in some cases, due to limitation on the subject or to uncertain efficacy. There is therefore a need for a new osteogenesis substance which serves as a prophylactic/therapeutic drug for osteoporosis, to increase once-decreased bone mass.

There are numerous benzopyran derivatives, such as those listed in the overview in the Progress in Medicinal Chemistry, Vol. 9, p. 65 (1973). That publication, however, does not describe the osteogenesis-promoting action of 4-oxo-4H-1-benzopyran-2-carboxamide derivatives. Nor is any such derivative known that has a substitutional group containing phosphonic acid as an N-substituent.

Also, European Patent Publication EP-524023-A1 describes the following compound as a therapeutic agent for osteoporosis.

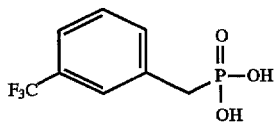

OBJECT OF THE INVENTION

This invention provides a benzopyran derivative which promotes osteogenesis, a method of production thereof and an osteogenesis promoter comprising it as an active ingredient.

SUMMARY OF THE INVENTION

The present inventors investigated the development of a more commonly applicable drug which acts directly on bone to promote osteogenesis, and found that a 4-oxo-4H-1-benzopyran-2-carboxamide derivative activates the osteoblast function directly involved in osteogenesis promotion, to promote bone calcification. The inventors made further investigations based on this finding, and developed the present invention.

Accordingly, the present invention relates to:
(1) a compound represented by the formula (I):

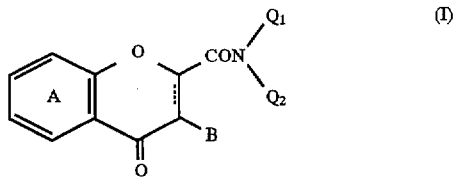

wherein B represents a hydrogen atom or a lower alkyl group; ring A represents a benzene ring which may have one or more substituents; ....... represents a single or double bond; $Q_1$ represents the group represented by the formula,

,or a hydrocarbon residue substituted with the group represented by the formula,

wherein X represents a bond or a spacer having a chain length of 1 to 4 atoms as the linear moiety which may have one or more side chains; $R^1$ and $R^2$, whether identical or not, independently represent a hydrogen atom or a lower alkyl, or may bind together to form a ring; $Q_2$, represents a hydrogen atom, a hydrocarbon residue which may be substiuted or a heterocyclic ring residue which may be substituted; or a salt thereof, (2) a method of producing a compound represented by the formula (I):

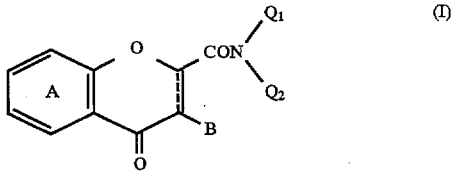

wherein B represents a hydrogen atom or a lower alkyl group; ring A represents a benzene ring which may have one or more substituents; ....... represents a single or double bond; $Q_1$ represents the group represented by the formula,

,or a hydrocarbon residue substituted with the group represented by the formula,

wherein X represents a bond or a spacer having a chain length of 1 to 4 atoms as the linear moiety which may have one or more side chains; $R^1$ and $R^2$, whether identical or not, independently represent a hydrogen atom or a lower alkyl, or may bind together to form a ring; $Q_2$ represents a hydrogen atom, a hydrocarbon residue which may be substituted or a heterocyclic ring residue which may be substituted; or a salt thereof, by comprising reacting a compound represented by the formula (II):

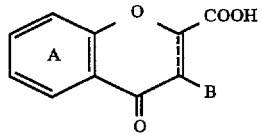

wherein B represents a hydrogen atom or a lower alkyl group; ....... represents a single or double bond; ring A represents a benzene ring which may have one or more substituents or reactive derivative thereof, and a compound represented by the formula (III):

wherein $Q'_1$ represents the group represented by the formula,

,or a hydrocarbon residue substituted with the group represented by the formula,

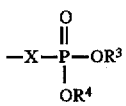

wherein X represents a bond or a spacer having a chains length of 1 to 4 atoms as the linear moiety which may have one or more side chains; $R^3$ and $R^4$, whether identical or not, independently represent a lower alkyl, or may bind together to form a ring; $Q_2$ is as defined above, and subsequently carrying out a phosphonic acid ester hydrolyzing reaction as necessary.

(3) an osteogenesis promoter comprising a compound represented by the formula (IV):

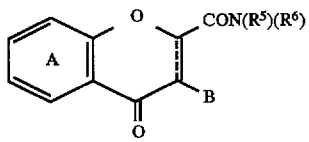

wherein $R^5$ and $R^6$, whether identical or not, independently represent a hydrogen atom, a phosphono group, a hydrocarbon residue which may be substituted or a heterocyclic ring residue which may be substituted; B represents a hydrogen atom or a lower alkyl group; ....... represents a single or double bond; ring A represents a benzene ring which may have one or more substituents, or a salt thereof, and (4) an osteogenesis promoter comprising a compound represented by the formula (I):

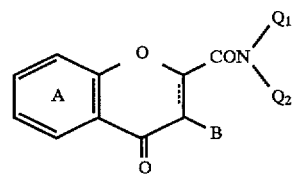

wherein B represents a hydrogen atom or a lower alkyl group; ring A represents a benzene ring which may have one or more substituents; ....... represents a single or double bond; $Q_1$ represents the group represented by the formula,

or a hydrocarbon residue substituted with the group represented by the formula,

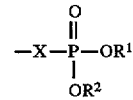

wherein X represents a bond or a spacer having a chain length of 1 to 4 atoms as the linear moiety which may have one or more side chains; $R^1$ and $R^2$, whether identical or not, independently represent a hydrogen atom or a lower alkyl, or may bind together to form a ring; $Q_2$ represents a hydrogen atom, a phosphono group, a hydrocarbon residue which may be substiuted or a heterocyclic ring residue which may be substituted; or a salt thereof.

DETAILED DESCRIPTION OF THE INVENTION

With respect to formulae (I), (II) and (IV), ring A represents a benzene ring which may have one or more substituents. The substituent is exemplified by halogen atoms, nitro groups, alkyls which may be substituted, hydroxyl groups which may be substituted, thiol groups which may be substituted, amino groups which may be substituted, acyls which may be substituted, carboxyl groups which may be esterified and aromatic cyclic groups which may be substituted.

The halogen atom as a substituent for ring A is exemplified by atoms of fluorine, chlorine, bromine and iodine, with preference given to fluorine and chlorine.

The alkyl as a substituent for ring A, which may be substituted, is exemplified by alkyls having 1 to 10 carbon atoms, whether linear or cyclic, including $C_{1-10}$ alkyls such as methyl, ethyl, propyl, isopropyl, butyl, isobutyl, sec-butyl, tert-butyl, pentyl, isopentyl, neopentyl, hexyl, heptyl, octyl, nonyl and decyl, with preference given to lower ($C_{1-6}$) alkyls, and $C_{3-7}$ cycloalkyls such as cyclopropyl, cyclobutyl, cyclopentyl, cyclohexyl and cycloheptyl. The substituent for said alkyl which may be substituted is exemplified by halogens (e.g., fluorine, chlorine, bromine and iodine), nitro groups, hydroxyl groups, thiol groups, amino groups and carboxyl groups.

The hydroxyl group as a substituent for ring A, which may be substituted, is exemplified by the hydroxyl group and hydroxyl groups having an appropriate substituent, specifically a substituent used as a hydroxyl group protecting group, such as alkoxys, alkenyloxys, aralkyloxys, acyloxys and aryloxys. Such alkoxys are preferably those having 1 to 10 carbon atoms (e.g., methoxy, ethoxy, propoxy, isopropoxy, butoxy, isobutoxy, sec-butoxy, tert-butoxy, pentyloxy, isopentyloxy, neopentyloxy, hexyloxy, heptyloxy, nonyloxy, cyclobutoxy, cyclopentyloxy and cyclohexyloxy), with greater preference given to those having 1 to 6 carbon atoms. Such alkenyloxys are preferably those having 2 to 10 carbon atoms, such as allyloxy, crotyloxy, 2-pentenyloxy, 3-hexenyloxy, 2-cyclopentenylmethoxy and 2-cyclohexenylmethoxy. Such aralkyloxys include phenyl-$C_{1-4}$ alkyloxys (e.g., benzyloxy and phenethyloxy). Such acyloxys are preferably alkanoyloxys having 2 to 4 carbon atoms (e.g., acetyloxy, propionyloxy, n-butyryloxy and isobutyryloxy). Such aryloxys include phenoxy and 4-chlorophenoxy.

The thiol group as a substituent for ring A, which may be substituted, is exemplified by the thiol group and thiol groups having an appropriate substituent, specifically a substituent used as a thiol group protecting group, such as alkylthios, aralkylthios and acylthios. Such alkylthios are preferably those having 1 to 10 carbon atoms (e.g., methylthio, ethylthio, propylthio, isopropylthio, butylthio, isobutylthio, sec-butylthio, tert-butylthio, pentylthio, isopentylthio, neopentylthio, hexylthio, heptylthio, nonylthio, cyclobutylthio, cyclopentylthio and cyclohexylthio). Such aralkylthios include phenyl-$C_{1-4}$ alkylthios (e.g., benzylthio and phenethylthio). Such acylthios are preferably alkanoylthios having 2 to 4 carbon atoms (e.g., acetylthio, propionylthio, butyrylthio and isobutyrylthio).

The substituent for said amino group as a substituent for ring A, which may be substituted, is exemplified by linear or cyclic alkyls having 1 to 10 carbon atoms, alkenyls having 2 to 10 carbon atoms, aromatic groups and acyl groups. One or two of these substituents may substitute for the amino group (—$NH_2$ group). Such alkyls include $C_{1-10}$ alkyls such as methyl, ethyl, isopropyl, butyl, isobutyl, sec-butyl, tert-butyl, pentyl, isopentyl, neopentyl, hexyl, heptyl, octyl, nonyl and decyl, with preference given to lower ($C_{1-6}$) alkyls, and $C_{3-7}$ cycloalkyls such as cyclopropyl, cyclobutyl, cyclopentyl, cyclohexyl and cycloheptyl. Such alkenyls include allyl, crotyl, 2-pentenyl, 3-hexenyl, 2-cyclopentenylmethyl and 2-cyclohexenylmethyl. Such aromatic groups include phenyl, naphthyl and anthryl. Such acyl groups include formyl and groups resulting from binding an alkyl having 1 to 10 carbon atoms, alkenyl having 2 to 10 carbon atoms or an aromatic group and a carbonyl group, including acetyl, propionyl, butyryl, isobutyryl, valeryl, isovaleryl, pivaloyl, hexanoyl, heptanoyl, octanoyl, cyclobutanoyl, cyclopentanoyl, cyclohexanoyl, cycloheptanoyl, crotonyl, 2-cyclohexenecarbonyl, benzoyl and nicotinoyl.

The acyl group as a substituent for ring A, which may be substituted, is exemplified by formyl and groups resulting from binding an alkyl having 1 to 10 carbon atoms, alkenyl having 2 to 10 carbon atoms or an aromatic group and a carbonyl group, including acetyl, propionyl, butyryl, isobutyryl, valeryl, isovaleryl, pivaloyl, hexanoyl, heptanoyl, octanoyl, cyclobutanoyl, cyclopentanoyl, cyclohexanoyl, cycloheptanoyl, crotonyl, 2-cyclohexenecarbonyl, benzoyl and nicotinoyl.

The esterified carboxyl group as a substituent for ring A is exemplified by lower alkoxycarbonyl groups and aryloxycarbonyl groups, with preference given to methoxycarbonyl, ethoxycarbonyl, propoxycarbonyl, phenoxycarbonyl and 1-naphthoxycarbonyl.

The aromatic cyclic group as a substituent for ring A, which may be substituted, is exemplified by $C_{6-14}$ aromatic hydrocarbon residues such as phenyl, naphthyl and anthryl, and heterocyclic aromatic residues such as pyridyl, furyl, thienyl, imidazolyl and thiazolyl. The substituent for said aromatic cyclic group which may be substituted is exemplified by halogen atoms, nitro groups, lower $C_{1-6}$ alkyls, hydroxyl groups, thiol groups, groups and carboxyl groups.

One to four of such substituents for ring A, whether identical or not, may substitute for the ring at any positions, and when they are adjacent to each other, they may bind together to form a ring represented by —$(CH_2)_m$— or —O—$(CH_2)_l$—O—, in which m and l represent an integer from 3 to 5 (preferably 2 or 3) and an integer from 1 to 3 (preferably 1 or 2), respectively.

With respect to formulae(I) and (III), the hydrocarbon residue for $Q_1$ and $Q'_1$, which are substituted with the groups represented by the formulae,

and

, respectively, is exemplified by aliphatic hydrocarbon residues, alicyclic hydrocarbon residues, alicyclic-aliphatic hydrocarbon residues, aromatic-aliphatic hydrocarbon residues, aromatic hydrocarbon residues and aromatic heterocyclic-aliphatic hydrocarbon residues. Such aliphatic hydrocarbon residues include saturated aliphatic hydrocarbon residues having 1 to 8 carbon atoms such as methyl, ethyl, propyl, isopropyl, butyl, isobutyl, sec-butyl, tert-butyl, pentyl, isopentyl, neopentyl, tert-pentyl, hexyl, isohexyl, heptyl and octyl, and unsaturated aliphatic hydrocarbon residues having 2 to 8 carbon atoms such as ethenyl, 1-propenyl, 2-propenyl, 1-butenyl, 2-butenyl, 3-butenyl, 2-methyl-1-propenyl, 1-pentenyl, 2-pentenyl, 3-pentenyl, 4-pentenyl, 3-methyl-2-butenyl, 1-hexenyl, 3-hexenyl, 2,4-hexadienyl, 5-hexenyl, 1-heptenyl, 1-octenyl, ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 3-hexynyl, 2,4-hexadiynyl, 5-hexynyl, 1-heptynyl and 1-octynyl. Such alicyclic hydrocarbon residues include saturated alicyclic hydrocarbon residues having 3 to 7 carbon atoms such as cyclopropyl, cyclobutyl, cyclopentyl, cyclohexyl and cycloheptyl, and unsaturated alicyclic hydrocarbon residues having 5 to 7 carbon atoms such as 1-cyclopentyl, 2-cyclopentyl, 3-cyclopentyl, 1-cyclohexenyl, 2-cyclohexenyl, 3-cyclohexenyl, 1-cycloheptenyl, 2-cycloheptenyl, 3-cycloheptenyl and 2,4-cycloheptadienyl. Such alicyclic-aliphatic hydrocarbon residues include those resulting from binding above-mentioned alicyclic hydrocarbon residues and aliphatic hydrocarbon residues to have 4 to 9 carbon atoms, such as cyclopropylmethyl, cyclopropylethyl, cyclobutylmethyl, cyclopentylmethyl, 2-cyclopentenylmethyl, 3-cyclopentenylmethyl, cyclohexylmethyl, 2-cyclohexenylmethyl, 3-cyclohexenylmethyl, cyclohexylethyl, cyclohexylpropyl, cycloheptylmethyl and cycloheptylethyl. Such aromatic-aliphatic hydrocarbon residues include phenylalkyls having 7 to 9 carbon atoms such as benzyl, phenethyl, 1-phenylethyl, 3-phenylpropyl, 2-phenylpropyl and 1-phenylpropyl, and naphthylalkyls having 11 to 13 carbon atoms such as α-naphthylmethyl, α-naphthylethyl, β-naphthylmethyl and β-naphthylethyl. Such aromatic hydrocarbon residues include phenyls and naphthyls (α-naphthyl, β-naphthyl). Such aromatic heterocyclicaliphatic hydrocarbon residue means those resulting from binding an aromatic heterocyclic ring residue and an aliphatic hydrocarbon residue. Said aromatic heterocyclic ring residue is exemplified by the same aromatic heterocyclic ring residues as specified for the heterocyclic ring residue for $R^5$ or $R^6$ below and said aliphatic hydrocarbon residue is exemplified by the same aliphatic hydrocarbon residues as specified above.

With respect to formulae (I) and (III), the hydrocarbon residue for $Q_1$ and $Q'_1$ may have, in addition to the group represented by the formula,

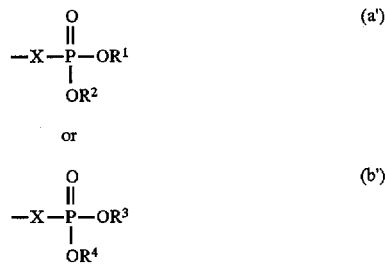

, 1 or 2 substituents at any positions thereon. Such substituents include aliphatic chain hydrocarbon groups, alicyclic hydrocarbon groups, aryl groups, aromatic heterocyclic groups, non-aromatic heterocyclic groups, halogen atoms, nitro groups, amino groups which may be substituted, acyl groups which may be substituted, hydroxyl groups which may be substituted, thiol groups which may be substituted, carboxyl groups which may be esterified and phosphono groups which may be esterified. Such aliphatic chain hydrocarbon groups include linear or branched aliphatic hydrocarbon groups such as alkyl groups, preferably those having 1 to 10 carbon atoms, alkenyl groups, preferably those having 2 to 10 carbon atoms, and alkynyl groups. Such alkyl groups include methyl, ethyl, propyl, isopropyl, butyl, isobutyl, sec-butyl, tert-butyl, pentyl, isopentyl, neopentyl, tert-pentyl, 1-ethylpropyl, hexyl, isohexyl, 1,1-dimethylbutyl, 2,2-dimethylbutyl, 3,3-dimethylbutyl, 2-ethylbutyl, hexyl, pentyl, octyl, nonyl and decyl. Such alkenyl groups include vinyl, allyl, isopropenyl, 1-propenyl, 2-methyl-1-propenyl, 1-butenyl, 2-butenyl, 3-butenyl, 2-ethyl-1-butenyl, 3-methyl-2-butenyl, 1-pentenyl, 2-pentenyl, 3-pentenyl, 4-pentenyl, 4-methyl-3-pentenyl, 1-hexenyl, 2-hexenyl, 3-hexenyl, 4-hexenyl and 5-hexenyl. Such alkynyl groups include ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl and 5-hexynyl. Such alicyclic hydrocarbon groups include saturated or unsaturated alicyclic hydrocarbons such as cycloalkyl groups, cycloalkenyl groups and cycloalkadienyl groups. Preferable cycloalkyl groups include cyclopropyl, cyclobutyl, cyclopentyl, cyclohexyl, cycloheptyl, cyclooctyl, bicyclo[2.2.1]heptyl, bicyclo[2.2.2]octyl, bicyclo[3.2.1]octyl, bicyclo[3.2.2]nonyl, bicyclo[3.3.1]nonyl, bicyclo[4.2.1]nonyl and bicyclo[4.3.1]decyl. Preferable cycloalkenyl groups include 2-cyclopenten-1-yl, 3-cyclopenten-1-yl, 2-cyclohexen-1-yl and 3-cyclohexen-1-yl. Preferable cycloalkadienyl groups include 2,4-cyclopentadien-1-yl, 2,4-cyclohexadien-1-yl and 2,5-cyclohexadien-1-yl. Such aryl groups are monocyclic or condensed polycyclic aromatic hydrocarbon groups, preferably phenyl, naphthyl, anthryl, phenanthryl, acenaphthylenyl and others, with preference given to phenyl, 1-naphthyl, 2-naphthyl and others. Preferable aromatic heterocyclic groups include aromatic monocyclic heterocyclic groups such as furyl, thienyl, pyrrolyl, oxazolyl, isoxazolyl, thiazolyl, isothiazolyl, imidazolyl, pyrazolyl, 1,2,3-oxadiazolyl, 1,2,4-oxadiazolyl, 1,3,4-oxadiazolyl, furazanyl, 1,2,3-thiadiazolyl, 1,2,4thiadiazolyl, 1,3,4-thiadiazolyl, 1,2,3-triazolyl, 1,2,4-triazolyl, tetrazolyl, pyridyl, pyridazinyl, pyrimidinyl, pyrazinyl and triazinyl, and aromatic condensed heterocyclic groups such as benzofuranyl, isobenzofuranyl, benzo[b]thienyl, indolyl, isoindolyl, 1H-indazolyl, benzimidazolyl, benzoxazolyl, 1,2-benzisoxazolyl, benzothiazolyl, 1,2-benzisothiazolyl, 1H-benzotriazolyl, quinolyl, isoquinolyl, cinnolinyl, quinazolinyl, quinoxalinyl, phthalazinyl, naphthylizinyl, purinyl, pteridinyl, carbazolyl, α-carbolinyl, β-carbolinyl, γ-carbolinyl, acridinyl, phenoxazinyl, phenothiazinyl, phenazinyl, phenoxthinyl, thianthrenyl, phenanthridinyl, phenanthrolinyl, indolizinyl, pyrrolo[1,2-b]pyridazinyl, pyrazolo[1,5-a]pyridyl, imidazo[1,2-a]pyridyl, imidazo[1,5-a]pyridyl, imidazo[1,2-b]pyridazinyl, imidazo[1,2-a]pyrimidinyl, 1,2,4-triazolo[4,3-a]pyridyl and 1,2,4-triazolo[4,3-b]pyridazinyl. Preferable non-aromatic heterocyclic groups include oxylanyl, azetidinyl, oxetanyl, thietanyl, pyrrolidinyl, tetrahydrofuryl, thiolanyl, piperizinyl, tetrahydropyranyl, morpholinyl, thiomorpholinyl and piperazinyl. Such halogens include fluorine, chlorine, bromine and iodine, with preference given to fluorine and chlorine. Said amino group which may be substituted include groups resulting from substitution of 1 or 2 of alkyls having 1 to 10 carbon atoms, alkenyls having 2 to 10 carbon atoms, aromatic groups or acyl groups having 2 to 10 atoms for the amino group ($-NH_2$ group) (e.g., methylamino, dimethylamino, ethylamino, diethylamino, dibutylamino, diallylamino, cyclohexylamino, phenylamino, N-methyl-N-phenylamino, acetylamino, propionylamino and benzoylamino). Said acyl group which may be substituted is exemplified by formyl and groups resulting from binding an alkyl having 1 to 10 carbon atoms, alkenyl having 2 to 10 carbon atoms or an aromatic group and a carbonyl group (e.g., acetyl, propionyl, butyryl, isobutyryl, valeryl, isovaleryl, pivaloyl, hexanoyl, heptanoyl, octanoyl, cyclobutanoyl, cyclopentanoyl, cyclohexanoyl, cycloheptanoyl, crotonyl, 2-cyclohexenecarbonyl, benzoyl and nicotinoyl). Said hydroxyl group which may be substituted is exemplified by the hydroxyl group and hydroxyl groups having an appropriate substituent, specifically a substituent used as a hydroxyl group protecting group, such as alkoxys, alkenyloxys, aralkyloxys, acyloxys and aryloxys. Such alkoxys are preferably those having 1 to 10 carbon atoms (e.g., methoxy, ethoxy, propoxy, isopropoxy, butoxy, isobutoxy, sec-butoxy, tert-butoxy, pentyloxy, isopentyloxy, neopentyloxy, hexyloxy, heptyloxy, nonyloxy, cyclobutoxy, cyclopentyloxy and cyclohexyloxy). Such alkenyloxys are preferably those having 2 to 10 carbon atoms, such as allyloxy, crotyloxy, 2-pentenyloxy, 3-hexenyloxy, 2-cyclopentenylmethoxy and 2-cyclohexenylmethoxy. Such aralkyloxys include phenyl-$C_{1-4}$alkyloxys (e.g., benzyloxy and phenethyloxy). Such acyloxys are preferably alkanoyloxys having 2 to 4 carbon atoms (e.g., acetyloxy, propionyloxy, butyryloxy and isobutyryloxy). Such aryloxys include phenoxy and 4-chlorophenoxy. Said thiol group which may be substituted is exemplified by the thiol group and thiol groups having an appropriate substituent, particularly a substituent for use as a thiol-protecting group, such as alkylthios, aralkylthios and acylthios. Such alkylthios are preferably alkylthios having 1 to 10 carbon atoms (e.g., methylthio, ethylthio, propylthio, isopropylthio, butylthio, isobutylthio, sec-butylthio, tert-butylthio, pentylthio, isopentylthio, neopentylthio, hexylthio, heptylthio, nonylthio, cyclobutylthio, cyclopentylthio and cyclohexylthio). Such aralkylthios include phenyl-$C_{1-4}$ alkylthios (e.g., benzylthio and phenethylthio). Such acylthios are preferably alkanoylthios having 2 to 4 carbon atoms (e.g., acetylthio, propionylthio, butyrylthio and isobutyrylthio). The ester of said carboxyl group which may be esterified is exemplified by those resulting from binding a carboxyl group and an alkyl group having 1 to 6 carbon atoms, such as methoxycarbonyl, ethoxycarbonyl, propoxycarbonyl, isopropoxycarbonyl, butoxycarbonyl, isobutoxycarbonyl, sec-butoxycarbonyl, tert-butoxycarbonyl, pentyloxycarbonyl and hexyloxycarbonyl, those resulting from binding a carboxyl group and an alkenyl group having 3 to 6 carbon atoms, such as allyloxycarbonyl, crotyloxycarbonyl, 2-pentenyloxycarbonyl and 3-hexenyloxycarbonyl, and those resulting from binding a carbonyl group and an aralkyl group, such as benzyloxycarbonyl and phenethyloxycarbonyl. Said phosphono group which may be esterified is exemplified by those represented by $P(O)(OR^9)(OR^{10})$ ($R^9$ and $R^{10}$, whether identical or not, independently represent a hydrogen atom or a lower alkyl, or may bind together to form a ring). The lower alkyl group for $R^9$ and 10 is exemplified by linear or branched lower alkyls having 1 to 6 carbon atoms (e.g., methyl, ethyl, propyl, isopropyl, butyl, isobutyl, sec-butyl, tert-butyl, pentyl, isopentyl, neopentyl and hexyl), and lower ($C_{3-7}$) cycloalkyls (e.g., cyclopropyl, cyclobutyl, cyclopentyl, cyclohexyl and cycloheptyl), with preference given to linear lower alkyls having 1 to 6 carbon atoms, more preferably lower alkyls having 1 to 3 carbon atoms. $R^9$ and $R^{10}$ may bind together to form a ring; for example, $R^9$ and $R^{10}$ may bind together to form —Z—(Z represents a carbon chain of 2 to 4 atoms in chain length which may have one or more side chains).

With respect to formulae (I) and (III) above, the substituent for the hydrocarbon residue for $Q_1$ and $Q'_1$, which may be substituted, may have 1 or more, preferably 1 to 3, appropriate substituents at any possible position. Such substituents include lower $C_{1-6}$ alkyls (e.g., methyl, ethyl, propyl, isopropyl, butyl, isobutyl, sec-butyl, tert-butyl, pentyl, isopentyl, neopentyl and hexyl), lower alkenyl groups (e.g., vinyl, allyl, isopropenyl, 1-propenyl, 2-methyl-1-propenyl, 1-butenyl, 2-butenyl, 3-butenyl, 2-ethyl-1-butenyl, 3-methyl-2-butenyl, 1-pentenyl, 2-pentenyl, 3-pentenyl, 4-pentenyl, 4-methyl-3-pentenyl, 1-hexenyl, 2-hexenyl, 3-hexenyl, 4-hexenyl and 5-hexenyl), lower alkynyl groups (e.g., ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl and 5-hexynyl), cycloalkyl groups (e.g., cyclopropyl, cyclobutyl, cyclopentyl, cyclohexyl and cycloheptyl), aryl groups (e.g., phenyl, 1-naphthyl and 2-naphthyl), aromatic heterocyclic groups, non-aromatic heterocyclic groups, aralkyl groups, amino groups, N-monosubstitutional amino groups (e.g., methylamino, ethylamino, cyclohexylamino and phenylamino), N,N-disubstitutional amino groups (e.g., dimethylamino, diethylamino, dibutylamino, diallylamino and N-methyl-N-phenylamino), amidino groups, acyl groups, carbamoyl groups, N-monosubstitutional carbamoyl groups (e.g., methylcarbamoyl, ethylcarbamoyl, cyclohexylcarbamoyl and phenylcarbamoyl), N,N-disubstitutional carbamoyl groups (e.g., dimethylcarbamoyl, diethylcarbamoyl, dibutylcarbamoyl, diallylcarbamoyl and N-methyl-N-phenylcarbamoyl), sulfamoyl groups, N-monosubstitutional sulfamoyl groups (e.g., methylsulfamoyl, ethylsulfamoyl, cyclohexylsulfamoyl and phenylsulfamoyl), N,N-disubstitutional sulfamoyl groups (e.g., dimethylsulfamoyl, diethylsulfamoyl, dibutylsulfamoyl, diallylsulfamoyl and N-methyl-N-phenylsulfamoyl), carboxyl groups, lower alkoxycarbonyl groups (e.g., methoxycarbonyl, ethoxycarbonyl, propoxycarbonyl, isopropoxycarbonyl, butoxycarbonyl, isobutoxycarbonyl, sec-butoxycarbonyl, tert-butoxycarbonyl, pentyloxycarbonyl and hexyloxycarbonyl), hydroxyl groups, lower alkoxy groups (e.g., methoxy, ethoxy, propoxy, isopropoxy, butoxy, isobutoxy, sec-butoxy, tert-butoxy and pentyloxy), lower alkenyloxy groups (e.g., allyloxycarbonyl, crotyloxycarbonyl, 2-pentenyloxycarbonyl and 3-hexenyloxycarbonyl), cycloalkyloxy groups (e.g., cyclopropyloxy, cyclobutyloxy, cyclopentyloxy, cyclohexyloxy and cycloheptyloxy), lower alkylthio groups (e.g., methylthio, ethylthio, propylthio, isopropylthio, butylthio, isobutylthio, sec-butylthio, tert-butylthio, pentylthio, isopentylthio, neopentylthio and hexylthio), aralkylthio groups, arylthio groups, sulfo groups, cyano groups, azide groups, halogen atoms fluorine, chlorine, bromine and iodine), nitro groups, nitroso groups, and phosphono groups which may be esterified. Such aralkyl groups include alkyl groups (e.g., methyl, ethyl, propyl, isopropyl, butyl, isobutyl, sec-butyl, tert-butyl, pentyl, isopentyl, neopentyl and hexyl) having an aryl group phenyl, 1-naphthyl and 2-naphthyl) as a substituent. Said aralkylthio group is a thiol group having an aralkyl group as a substituent, which aralkyl group is exemplified by the seine as those specified above. Said arylthio is exemplified by thiol groups having an aryl group (e.g., phenyl, 1-naphthyl and 2-naphthyl) as a substituent. Said aromatic heterocyclic group, non-aromatic heterocyclic group, acyl or phosphono group which may be esterified is exemplified by the same substituents as specified for the hydrocarbon residue for $Q_1$ and $Q'_1$ above.

With respect to formula (I), it is preferable that $Q_1$ be an aromatic hydrocarbon residue (preferably an aryl group (e.g. phenyl)) which is substituted with the group represented by the formula,

,with greater preference given to one represented by the following formula:

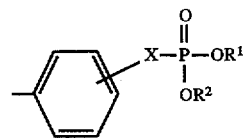

wherein X, $R^1$ and $R^2$ have the same definitions as below.

With respect to formula (III), it is preferable that $Q'_1$ be an aromatic hydrocarbon residue (preferably an aryl group (e.g. phenyl)) which is substituted with the group represented by the formula,

,with greater preference given to one represented by the following formula:

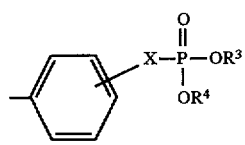

wherein X, $R^3$ and $R^4$ have the same definitions as below.

With respect to formulae (I) and (III), the hydrocarbon residue for $Q_2$ is exemplified by the same hydrocarbon residue as specified for $R^5$ and $R^6$ below.

With respect to formulae (I) and (III), the heterocyclic ring residue for $Q_2$ is exemplified by the same heterocyclic ring residue as specified for $R^5$ and $R^6$ below.

With respect to formulae (I) and (III), the substituent for the hydrocarbon residue and the heterocyclic ring residue as a substituent for $Q_2$ is exemplified by the same substituent as specified for $R^5$ and $R^6$ below.

With respect to formulae (I) and (III), it is preferable that $Q_2$ be a hydrogen atom, or a lower alkyl having 1 to 6 carbon atoms (e.g., methyl, ethyl, propyl, isopropyl, butyl, isobutyl, sec-butyl, tert-butyl, pentyl, isopentyl, neopentyl and hexyl), and a lower ($C_{3-7}$) cycloalkyl (e.g., cyclopropyl, cyclobutyl, cyclopentyl, cyclohexyl and cycloheptyl). Preference is given to a hydrogen atom or a lower $C_{1-6}$ alkyl, with greater preference given to a hydrogen atom or a $C_{1-3}$ alkyl.

With respect to general formulas (I), (II) and (IV), the lower alkyl group for B is exemplified by linear or branched lower alkyls having 1 to 4 carbon atoms (e.g., methyl, ethyl, propyl, isopropyl, butyl, isobutyl, sec-butyl and tert-butyl), with preference given to methyl and ethyl.

With respect to formulae (a') and (b'), the spacer having a chain length of 1 to 4 atoms as the linear moiety for X, which may have one or more side chains, may be any one, as long as it is a divalent chain whose linear chain moiety consists of 1 to 4 atoms, and may have one or more side chains. The divalent chain constituting said linear chain moiety is exemplified by alkylene chains represented by —$(CH_2)_{k1}$— ($k_1$ is an integer from 1 to 4) and alkenylene chains represented by —$(CH_2)_{k2}$—(CH=CH)—$(CH_2)_{k3}$— ($k_2$ and $K_3$, whether identical or not, independently are 0, 1 or 2, provided that the sum of $k_2$ and $k_3$ is not more than 4. Said side chain may be any one, as long as it is capable of binding to the divalent chain constituting the linear chain moiety, exemplified by lower $C_{1-6}$) alkyls (e.g. methyl, ethyl, propyl, isopropyl, butyl, isobutyl, sec-butyl, tert-butyl, pentyl, isopentyl, neopentyl and hexyl), lower ($C_{3-7}$) cycloalkyls (e.g. cyclopropyl, cyclobutyl, cyclopentyl, cyclohexyl and cycloheptyl), phosphono groups which may be esterified and carboxyl groups which may be esterified. Said phosphono group which may be esterified is exemplified by those represented by $P(O)(OR^{11})(OR^{12})$ ($R^{11}$ and $R^{12}$ have the same definitions as specified for $R^1$ and $R^2$). The ester of said carboxyl group which may be esterified is exemplified by those resulting from binding a carboxyl group and a lower ($C_{1-6}$) alkyl group, such as methoxycarbonyl, ethoxycarbonyl, propoxycarbonyl, isopropoxycarbonyl, butoxycarbonyl, isobutoxycarbonyl, sec-butoxycarbonyl, tert-butoxycarbonyl, pentyloxycarbonyl and hexyloxycarbonyl.

With respect to formulae (a) and (a'), the lower alkyl group for $R^1$ and $R^2$ is exemplified by linear or branched lower alkyls having 1 to 6 carbon atoms (e.g., methyl, ethyl, propyl, isopropyl, butyl, isobutyl, sec-butyl, tert-butyl, pentyl, isopentyl, neopentyl and hexyl), and lower ($C_{3-7}$) cycloalkyls (e.g., cyclopropyl, cyclobutyl, cyclopentyl, cyclohexyl and cycloheptyl), with preference given to linear lower alkyls having 1 to 6 carbon atoms, more preferably lower alkyls having 1 to 3 carbon atoms. $R^1$ and $R^2$ may bind together to form a ring; for example, $R^1$ and $R^2$ may bind together to form —Z—(Z represents a carbon chain of 2 to 4 atoms in chain length which may have one or more side chains).

With respect to formulae (b) and (b'), the lower alkyl group for $R^3$ and $R^4$ is exemplified by linear or branched lower alkyls having 1 to 6 carbon atoms (e.g., methyl, ethyl, propyl, isopropyl, butyl, isobutyl, sec-butyl, tert-butyl, pentyl, isopentyl, neopentyl and hexyl), and lower ($C_{3-7}$) cycloalkyls (e.g., cyclopropyl, cyclobutyl, cyclopentyl, cyclohexyl and cycloheptyl). Preference is given to linear lower alkyls having 1 to 6 carbon atoms, with greater preference given to lower alkyls having 1 to 8 carbon atoms. $R^3$ and $R^4$ may bind together to form a ring; for example, $R^3$ and $R^4$ may bind together to form —Z—(Z represents a carbon chain of 2 to 4 atoms in chain length which may have one or more side chains).

The spacer for Z is exemplified by the same spacers as specified for X but comprising a carbon chain of 2 to 4 atoms in chain length, including those resulting from binding $R^1$ and $R^2$, $R^3$ and $R^4$ or $R^9$ and $R^{10}$, such as —$(CH_2)_2$—, —$(CH_2)_3$—, —$(CH_2)_4$—, —$CH(CH_3)$—$CH_2$—, —$CH(CH_3)$—$CH(CH_3)$—, —$CH_2C(CH_3)_2$—$CH_2$—, —$CH_2$—$CH(C_2H_5)$—$CH_2$— and —$CH(CH_3)$—$CH_2$—$CH(CH_3)$—. The side chains for Z include lower $C_{1-4}$ alkyls such as methyl, ethyl, propyl, isopropyl, butyl, isobutyl, sec-butyl, tert-butyl.

With respect to general formula (IV) above, the hydrocarbon residue for $R^5$ and $R^6$ which may be substituted is exemplified by aliphatic hydrocarbon residues, alicyclic hydrocarbon residues, alicyclic-aliphatic hydrocarbon residues, aromatic-aliphatic hydrocarbon residues, aromatic hydrocarbon residues and aromatic heterocyclic-aliphatic hydrocarbon residues. Such aliphatic hydrocarbon residues include saturated aliphatic hydrocarbon residues having 1 to 8 carbon atoms such as methyl, ethyl, propyl, isopropyl, butyl, isobutyl, sec-butyl, tert-butyl, pentyl, isopentyl, neopentyl, tert-pentyl, hexyl, isohexyl, heptyl and octyl, and unsaturated aliphatic hydrocarbon residues having 2 to 8 carbon atoms such as ethenyl, 1-propenyl, 2-propenyl, 1-butenyl, 2-butenyl, 3-butenyl, 2-methyl-1-propenyl, 1-pentenyl, 2-pentenyl, 3-pentenyl, 4-pentenyl, 3-methyl-2-butenyl, 1-hexenyl, 3-hexenyl, 2,4-hexadienyl, 5-hexenyl, 1-heptenyl, 1-octenyl, ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 3-hexynyl, 2,4-hexadiynyl, 5-hexynyl, 1-heptynyl and 1-octynyl. Such alicyclic hydrocarbon residues include saturated alicyclic hydrocarbon residues having 3 to 7 carbon atoms such as cyclopropyl, cyclobutyl, cyclopentyl, cyclohexyl and cycloheptyl, and unsaturated alicyclic hydrocarbon residues having 5 to 7 carbon atoms such as 1-cyclopentenyl, 2-cyclopentenyl, 3-cyclopentenyl, 1-cyclohexenyl, 2-cyclohexenyl, 3-cyclohexenyl, 1-cycloheptenyl, 2-cycloheptenyl, 3-cycloheptenyl and 2,4-cycloheptadienyl. Such alicyclic-aliphatic hydrocarbon residues include those resulting from binding above-mentioned alicyclic hydrocarbon residues and aliphatic hydrocarbon residues to have 4 to 9 carbon atoms, such as cyclopropylmethyl, cyclopropylethyl, cyclobutylmethyl, cyclopentylmethyl, 2-cyclopentenylmethyl, 3-cyclopentenylmethyl, cyclohexylmethyl, 2-cyclohexenylmethyl, 3-cyclohexenylmethyl, cyclohexylethyl, cyclohexylpropyl, cycloheptylmethyl and cycloheptylethyl. Such aromatic-aliphatic hydrocarbon residues include phenylalkyls having 7 to 9 carbon atoms such as benzyl, phenetyl, 1-phenylethyl, 3-phenylpropyl, 2-phenylpropyl and 1-phenylpropyl, and naphthylalkyls having 11 to 13 carbon atoms such as α-naphthylmethyl, α-naphthylethyl, β-naphthylmethyl and β-naphthylethyl. Such aromatic hydrocarbon residues include phenyls and naphthyls (α-naphthyl, β-naphthyl). Such aromatic heterocyclic-aliphatic hydrocarbon residue means those resulting from binding an aromatic heterocyclic ring residue and an aliphatic hydrocarbon residue. Said aromatic heterocyclic ring residue is exemplified by the same aromatic heterocyclic ring residues as specified for the heterocyclic ring residue for $R^5$ and $R^6$ below and said aliphatic hydrocarbon residue is exemplified by the same aliphatic hydrocarbon residues as specified above.

With respect to formula (IV), the heterocyclic ring residue for $R^5$ and $R^6$, which may be substituted, is exemplified by 5- to 7-membered heterocyclic ring residues containing 1 atom of sulfur, nitrogen or oxygen, 5- or 6-membered heterocyclic ring residues containing 2 to 4 atoms of nitrogen and 5- or 6-membered heterocyclic ring residues containing 1 or 2 atoms of nitrogen and 1 atom of sulfur or oxygen. These heterocyclic ring residues may have condensed with a 6-membered ring containing 2 or fewer atoms of nitrogen, a benzene ring or a 5-membered ring containing 1 atom of sulfur. Said heterocyclic ring residue is preferably an aromatic heterocyclic ring residue, exemplified by 2-pyridyl, 3-pyridyl, 4-pyridyl, 2-pyrimidinyl, 4-pyrimidinyl, 5-pyrimidinyl, 6-pyrimidinyl, 3-pyridazinyl, 4-pyridazinyl, 2-pyrazinyl, 2-pyrrolyl, 3-pyrrolyl, 2-imidazolyl, 4-imidazolyl, 5-imidazolyl, pyrazolyl, 4-pyrazolyl, isothiazolyl, isoxazolyl, 2-thiazolyl, 4-thiazolyl, 5-thiazolyl, 2-oxazolyl, 4-oxazolyl, 5-oxazolyl, 1,2,4-triazol-3-yl, 1,2,3-triazol-4-yl, tetrazol-5-yl, benzimidazol-2-yl, indol-3-yl, benzopyrazol-3-yl, 1H-pyrrolo[2,3-b]pyradin-2-yl, 1H-pyrrolo[2,3-b]pyridin-6-yl, 1H-imidazo[4,5-b]pyridin-2-yl, 1H-imidazo[4,5-c]pyridin-2-yl and 1H-imidazo[4,5-b]pyrazin-2-yl.

With respect to formula (IV) above, the phosphono group for $R^5$ or $R^6$ is represented by $P(O)(OR^7)(OR^8)$ ($R^7$ and $R^8$, whether identical or not, independently represent a hydrogen atom or lower alkyl, or may bind together to form a ring). The lower alkyl group for $R^7$ or $R^8$ is exemplified by linear or branched lower alkyls having 1 to 6 carbon atoms (e.g., methyl, ethyl, propyl, isopropyl, butyl, isobutyl, sec-butyl, tert-butyl, pentyl, isopentyl, neopentyl and hexyl), and lower ($C_{3-7}$) cycloalkyls (e.g., cyclopropyl, cyclobutyl, cyclopentyl, cyclohexyl and cycloheptyl), with preference given to linear lower alkyls having 1 to 6 carbon atoms, with greater preference given to lower alkyls having 1 to 3 carbon atoms. $R^7$ and $R^8$ may bind together to form a ring; for example, $R^7$ and $R^8$ may bind together to form —$(CH_2)_2$—, —$(CH_2)_3$—, —$(CH_2)_4$—, —$CH(CH_3)$—$CH_2$—, —$CH(CH_3)$—$CH(CH_3)$—, —$CH_2$—$C(CH_3)_2$—$CH_2$—, —$CH_2$—$CH(C_2H_5)$—$CH_2$— and —$CH(CH_3)$—$CH_2$—$CH(CH_3)$—.

With respect to general formula (IV) above, the hydrocarbon residue or heterocyclic ring residue for $R^5$ and $R^6$ may have 1 to 3 substituents at any positions thereon. Such substituents include aliphatic chain hydrocarbon groups, alicyclic hydrocarbon groups, aryl groups, aromatic heterocyclic groups, non-aromatic heterocyclic groups, halogen atoms, nitro groups, groups which may be substituted, acyl groups which may be substituted, hydroxyl groups which may be substituted, thiol groups which may be substituted, carboxyl groups which may be esterified and phosphono groups which may be esterified. Such aliphatic chain hydrocarbon groups include linear or branched aliphatic hydrocarbon groups such as alkyl groups, preferably those having 1 to 10 carbon atoms, alkenyl groups, preferably those having 2 to 10 carbon atoms, and alkynyl groups. Such alkyl groups include methyl, ethyl, propyl, isopropyl, butyl, isobutyl, sec-butyl, tert-butyl, pentyl, isopentyl, neopentyl, tert-pentyl, 1-ethylpropyl, hexyl, isohexyl, 1,1-dimethylbutyl, 2,2-dimethylbutyl, 3,3-dimethylbutyl, 2-ethylbutyl, hexyl, pentyl, octyl, nonyl and decyl. Such alkenyl groups include vinyl, allyl, isopropenyl, 1-propenyl, 2-methyl-1-propenyl, 1-butenyl, 2-butenyl, 3-butenyl, 2-ethyl-1-butenyl, 3-methyl-2-butenyl, 1-pentenyl, 2-pentenyl, 3-pentenyl, 4-pentenyl, 4-methyl-3-pentenyl, 1-hexenyl, 2-hexenyl, 3-hexenyl, 4-hexenyl and 5-hexenyl. Such alkynyl groups include ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl and 5-hexynyl. Such alicyclic hydrocarbon groups include saturated or unsaturated alicyclic hydrocarbons such as cycloalkyl groups, cycloalkenyl groups and cycloalkadienyl groups. Preferable cycloalkyl groups include cyclopropyl, cyclobutyl, cyclopentyl, cyclohexyl, cycloheptyl, cyclooctyl, bicyclo[2.2.1]heptyl, bicyclo[2.2.2]octyl, bicyclo[3.2.1]octyl, bicyclo[3.2.2]nonyl, bicyclo[3.3.1]nonyl, bicyclo[4.2.1]nonyl and bicyclo[4.3.1]decyl. Preferable cycloalkenyl groups include 2-cyclopenten-1-yl, 3-cyclopenten-1-yl, 2-cyclohexen-1-yl and 3-cyclohexen-1-yl. Preferable cycloalkadienyl groups include 2,4-cyclopentadien-1-yl, 2,4-cyclohexadien-1-yl and 2,5-cyclohexadien-1-yl. Such aryl groups are monocyclic or condensed polycyclic aromatic hydrocarbon groups, preferably phenyl, naphthyl, anthryl, phenanthryl, acenaphthylenyl and others, with preference given to phenyl, 1-naphthyl, 2-naphthyl and others. Preferable aromatic heterocyclic groups include aromatic monocyclic heterocyclic groups such as furyl, thienyl, pyrrolyl, oxazolyl, isoxazolyl, thiazolyl, isothiazolyl, imidazolyl, pyrazolyl, 1,2,3-oxadiazolyl, 1,2,4-oxadiazolyl, 1,3,4-oxadiazolyl, furazanyl, 1,2,3-thiadiazolyl, 1,2,4-thiadiazolyl, 1,3,4-thiadiazolyl, 1,2,3-triazolyl, 1,2,4-triazolyl, tetrazolyl, pyridyl, pyridazinyl, pyrimidinyl, pyrazinyl and triazinyl, and aromatic condensed heterocyclic groups such as benzofuranyl, isobenzofuranyl, benzo[b]thienyl, indolyl, isoindolyl, 1H-indazolyl, benzimidazolyl, benzoxazolyl, 1,2-benzisoxazolyl, benzothiazolyl, 1,2-benzisothiazolyl, 1H-benzotriazolyl, quinolyl, isoquinolyl, cinnolinyl, quinazolinyl, quinoxalinyl, phthalazinyl, naphthylizinyl, purinyl, pteridinyl, carbazolyl, α-carbolinyl, β-carbolinyl, γ-carbolinyl, acridinyl, phenoxazinyl, phenothiazinyl, phenazinyl, phenoxthinyl, thianthrenyl, phenanthridinyl, phenanthrolinyl, indolizinyl, pyrrolo[1,2-b]pyridazinyl, pyrazolo[1,5-a]pyridyl, imidazo[1,2-a]pyridyl, imidazo[1,5-a]pyridyl, imidazo[1,2-b]pyridazinyl, imidazo[1,2-a]pyrimidinyl, 1,2,4-triazolo[4,3-a]pyridyl and 1,2,4-triazolo[4,3-b]pyridazinyl. Preferable non-aromatic heterocyclic groups include oxylanyl, azetidinyl, oxetanyl, thietanyl, pyrrolidinyl, tetrahydrofuryl, thiolanyl, piperizinyl, tetrahydropyranyl, morpholinyl, thiomorpholinyl and piperazinyl. Such halogens include fluorine, chlorine, bromine and iodine, with preference given to fluorine and chlorine. Said amino group which may be substituted include groups resulting from substitution of 1 or 2 of alkyls having 2 to 10 carbon atoms, alkenyls having 1 to 10 carbon atoms, aromatic groups or acyl groups having 2 to 10 atoms for the amino group (—$NH_2$ group) (e.g., methylamino, dimethylamino, ethylamino, diethylamino, dibutylamino, diallylamino, cyclohexylamino, phenylamino, N-methyl-N-phenylamino, acetylamino, propionylamino and benzoylamino). Said acyl group which may be substituted is exemplified by formyl and groups resulting from binding an alkyl having 2 to 10 carbon atoms, alkenyl having 1 to 10 carbon atoms or an aromatic group and a carbonyl group (e.g., acetyl, propionyl, butyryl, isobutyryl, valeryl, isovaleryl, pivaloyl, hexanoyl, heptanoyl, octanoyl, cyclobutanoyl, cyclopentanoyl, cyclohexanoyl, cycloheptanoyl, crotonyl, 2-cyclohexenecarbonyl, benzoyl and nicotinoyl). Said hydroxyl group which may be substituted is exemplified by the hydroxyl group and hydroxyl groups having an appropriate substituent, specifically a substituent used as a hydroxyl group protecting group, such as alkoxys, alkenyloxys, aralkyloxys, acyloxys and aryloxys. Such alkoxys are preferably those having 1 to 10 carbon atoms (e.g., methoxy, ethoxy, propoxy, isopropoxy, butoxy, isobutoxy, sec-butoxy, tert-butoxy, pentyloxy, isopentyloxy, neopentyloxy, hexyloxy, heptyloxy, nonyloxy, cyclobutyloxy, cyclopentyloxy and cyclohexyloxy). Such alkenyloxys are preferably those having 1 to 10 carbon atoms, such as allyloxy, crotyloxy, 2-pentenyloxy, 3-hexenyloxy, 2-cyclopentenylmethoxy and 2-cyclohexenylmethoxy. Such aralkyloxys include phenyl-$C_{1-4}$ alkyloxys (e.g., benzyloxy and phenethyloxy). Such acyloxys are preferably alkanoyloxys having 2 to 4 carbon atoms (e.g., acetyloxy, propionyloxy, butyryloxy and isobutyryloxy). Such aryloxys include phenoxy and 4-chlorophenoxy. Said thiol group which may be substituted is exemplified by the thiol group and thiol groups having an appropriate substituent, particularly a substituent for use as a thiol-protecting group, such as alkylthios, aralkylthios and acylthios. Such alkylthios are preferably alkylthios having 1 to 10 carbon atoms (e.g., methylthio, ethylthio, propylthio, isopropylthio, butylthio, isobutylthio, sec-butylthio, tert-butylthio, pentylthio, isopentylthio, neopentylthio, hexylthio, heptylthio, nonylthio, cyclobutylthio, cyclopentylthio and cyclohexylthio). Such aralkylthios include phenyl-$C_{1-4}$ alkylthios (e.g., benzylthio and phenethylthio). Such acylthios are preferably alkanoylthios having 2 to 4 carbon atoms (e.g., acetylthio, propionylthio, butyrylthio and isobutyrylthio). The ester of said carboxyl group which may be esterified is exemplified by those resulting from binding a carboxyl group and an alkyl group having 1 to 6 carbon atoms, such as methoxycarbonyl, ethoxycarbonyl, propoxycarbonyl, isopropoxycarbonyl, butoxycarbonyl, isobutoxycarbonyl, sec-butoxycarbonyl, tert-butoxycarbonyl, pentyloxycarbonyl and hexyloxycarbonyl, those resulting from binding a carboxyl group and an alkenyl group having 3 to 6 carbon atoms, such as allyloxycarbonyl, crotyloxycarbonyl, 2-pentenyloxycarbonyl and 3-hexenyloxycarbonyl, and those resulting from binding a carbonyl group and an aralkyl group, such as benzyloxycarbonyl and phenethyloxycarbonyl. Said phosphono group which may be esterified is exemplified by those represented by $P(O)(OR^1)(OR^2)$ ($R^1$ and $R^2$ have the same definitions as above).

With respect to formula (IV) above, the substituent for the hydrocarbon residue or heterocyclic ring residue represented by $R^5$ or $R^6$, each of which may be substituted, may have 1 or more, preferably 1 to 3, appropriate substituents at any possible position. Such substituents include lower $C_{1-6}$) alkyls (e.g., methyl, ethyl, propyl, isopropyl, butyl, isobutyl, sec-butyl, tert-butyl, pentyl, isopentyl, neopentyl and hexyl), lower alkenyl groups (e.g., vinyl, allyl, isopropenyl, 1-propenyl, 2-methyl-1-propenyl, 1-butenyl, 2-butenyl, 3-butenyl, 2-ethyl-1-butenyl, 3-methyl-2-butenyl, 1-pentenyl, 2-pentenyl, 3-pentenyl, 4-pentenyl, 4-methyl-3-pentenyl, 1-hexenyl, 2-hexenyl, 3-hexenyl, 4-hexenyl and 5-hexenyl), lower alkynyl groups (e.g., ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl and 5-hexynyl), cycloalkyl groups (e.g., cyclopropyl, cyclobutyl, cyclopentyl, cyclohexyl and cycloheptyl), aryl groups (e.g., phenyl, 1-naphthyl and 2-naphthyl), aromatic heterocyclic groups, non-aromatic heterocyclic groups, aralkyl groups, amino groups, N-monosubstitutional amino groups (e.g., methylamino, ethylamino, cyclohexylamino and phenylamino), N,N-disubstitutional amino groups (e.g., dimethylamino, diethylamino, dibutylamino, diallylamino and N-methyl-N-phenylamino), amidino groups, acyl groups, carbamoyl groups, N-monosubstitutional carbamoyl groups (e.g., methylcarbamoyl, ethylcarbamoyl, cyclohexylcarbamoyl and phenylcarbamoyl), N,N-disubstitutional carbamoyl groups (e.g., dimethylcarbamoyl, diethylcarbamoyl, dibutylcarbamoyl, diallylcarbamoyl and N-methyl-N-phenylcarbamoyl), sulfamoyl groups, N-monosubstitutional sulfamoyl groups (e.g., methylsulfamoyl, ethylsulfamoyl, cyclohexylsulfamoyl and phenylsulfamoyl), N,N-disubstitutional sulfamoyl groups (e.g., dimethylsulfamoyl, diethylsulfamoyl, dibutylsulfamoyl, diallylsulfamoyl and N-methyl-N-phenylsulfamoyl), carboxyl groups, lower alkoxycarbonyl groups (e.g., methoxycarbonyl, ethoxycarbonyl, propoxycarbonyl, isopropoxycarbonyl, butoxycarbonyl, isobutoxycarbonyl, sec-butoxycarbonyl, tert-butoxycarbonyl, pentyloxycarbonyl and hexyloxycarbonyl), hydroxyl groups, lower alkoxy groups (e.g., methoxy, ethoxy, propoxy, isopropoxy, butoxy, isobutoxy, sec-butoxy, tert-butoxy and pentyloxy), lower alkenyloxy groups (e.g., allyloxycarbonyl, crotyloxycarbonyl, 2-pentenyloxycarbonyl and 3-hexenyloxycarbonyl), cycloalkyloxy groups (e.g., cyclopropyloxy, cyclobutyloxy, cyclopentyloxy, cyclohexyloxy and cycloheptyloxy), lower alkylthio groups (e.g., methylthio, ethylthio, propylthio, isopropylthio, butylthio, isobutylthio, sec-butylthio, tert-butylthio, pentylthio, isopentylthio, neopentylthio and hexylthio), aralkylthio groups, arylthio groups, sulfo groups, cyano groups, azide groups, halogen atoms (e.g., fluorine, chlorine, bromine and iodine), nitro groups, nitroso groups, and phosphono groups which may be esterified. Such aralkyl groups include alkyl groups (e.g., methyl, ethyl, propyl, isopropyl, butyl, isobutyl, sec-butyl, tert-butyl, pentyl, isopentyl, neopentyl and hexyl) having an aryl group (e.g., phenyl, 1-naphthyl and 2-naphthyl) as a substituent. Said aralkylthio group is a thiol group having an aralkyl group as a substituent, which aralkyl group is exemplified by the same as those specified above. Said arylthio is exemplified by thiol groups having an aryl group (e.g., phenyl, 1-naphthyl and 2-naphthyl) as a substituent. Said aromatic heterocyclic group, non-aromatic heterocyclic group, acyl or phosphono group which may be esterified is exemplified by the same substituents as specified for the hydrocarbon residue or heterocyclic ring reside represented by $R^5$ or $R^6$ above. With respect to general formulae (I), (II) and (IV) above, ring A is preferably a benzene ring which is not substituted or which has one or more substituents selected from the group of halogen atoms, alkyl groups and alkoxy groups as substituent.

With respect to general formula (IV) above, it is preferable that either $R^5$ or $R^6$ be an aromatic hydrocarbon residue or aromatic heterocyclic ring residue which may be substituted, more preferably an aryl group which may be substituted. Said aryl group is preferably a phenyl, with greater preference given to one represented by the following general formula:

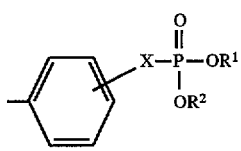

wherein X, $R^1$ and $R^2$ have the same definitions as above.
Examples of the compounds of the invention are as follows:

N-(4-diethoxyphosphorylmethylphenyl)-4-oxo-4H-1-benzopyran-2-carboxamide

N-(4-dimethoxyphosphorylmethylphenyl)-4-oxo-4H-1-benzopyran-2-carboxamide

N-(4-ethylenedioxyphosphorylmethylphenyl)-4-oxo-4H-1-benzopyran-2-carboxamide

N-(4-trimethylenedioxyphosphorylmethylphenyl)-4-oxo-4H-1-benzopyran-2-carboxamide N-(4-diethoxyphosphorylphenyl)-4-oxo-4H-1-benzopyran-2-carboxamide N-(4-dimethoxyphosphorylphenyl)-4-oxo-4H-1-benzopyran-2-carboxamide N-(4-ethylenedioxyphosphorylphenyl)-4oxo-4H-1-benzopyran-2-carboxamide N-(4-trimethylenedioxyphosphorylphenyl)-4-oxo-4H-benzopyran-2-carboxamide N-(2-diethoxyphosphorylmethylphenyl)-4-oxo-4H-1-benzopyran-2-carboxamide N-(3-dimethoxyphosphorylmethylphenyl)-4-oxo-4H-1-benzopyran-2-carboxamide N-[4-(2-dimethoxyphosphorylethyl)phenyl]-4-oxo-4H-1-benzopyran-2-carboxamide N-(3-diethoxyphosphorylpropyl)-4-oxo-4H-1-benzopyran-2-carboxamide N-(4-dimethoxyphosphorylmethylphenyl)-N-methyl-4-oxo-4H-1-benzopyran-2-carboxamide N-(4-phosphonomethylphenyl)-4-oxo-4H-1-benzopyran-2-carboxamide N-(4-diethoxyphosphorylmethylphenyl)-6,7-dimethyl-4-oxo-4H-1-benzopyran-2-carboxamide N-(4-dimethoxyphosphorylmethylphenyl)-6,7-methylenedioxy-4-oxo-4H-1-benzopyran-2-carboxamide 6-chloro-N-(4-diethoxyphosphorylmethylphenyl)-4-oxo-4H-1-benzopyran-2-carboxamide N-(4-diethoxyphosphorylmethylphenyl)-3-methyl-4-oxo-4H-1-benzopyran-2-carboxamide N-(4-dimethoxyphosphorylmethylphenyl)-3-methyl-4-oxo-4H-1-benzopyran-2-carboxamide N-(4-diethoxyphosphorylmethylphenyl)-2,3-dihydro-4-oxo-4H-1-benzopyran-2-carboxamide 2,3-dihydro-N-(4-dimethoxyphosphorylmethylphenyl)-4-oxo-4H-1-benzopyran-2-carboxamide The salt of the compound of general formulae (I) and (IV) is preferably a pharmaceutically acceptable salt, exemplified by salts with inorganic bases, salts with organic bases, salts with inorganic adds, salts with organic acids and salts with basic or acidic amino acids. Preferable salts with inorganic bases include alkali metal salts such as sodium salt and potassium salt, alkaline earth metal salts such as calcium salt and magnesium salt, aluminum salt and ammonium salt. Preferable salts with organic bases include salts with trimethylamine, triethylamine, pyridine, picoline, ethanolamine, diethanolamine, triethanolamine, dicyclohexylamine and N,N'-dibenzylethylenediamine. Preferable salts with inorganic acids include salts with hydrochloric acid, hydrobromic acid, nitric acid, sulfuric acid and phosphoric acid. Preferable salts with organic acids include salts with formic acid, acetic acid, trifluoroacetic acid, fumaric acid, oxalic acid, tartaric acid, maleic acid, citric acid, succinic acid, malic acid, methanesulfonic acid, benzenesulfonic acid and p-toluenesulfonic acid. Preferable salts with basic amino acids include salts with arginine, lysine and ornithine. Preferable salts with acidic amino acids include salts with aspartic acid and glutamic acid.

The compound represented by general formulae (I) and (IV) can be administered orally or non-orally, as formulated with a pharmaceutically acceptable carrier, in the form of solid preparations such as tablets, capsules, granules and powders, or liquid preparations such as syrups and injectable preparations.

Pharmaceutically acceptable carriers are various organic or inorganic carrier substances in common use as pharmaceutical materials, including excipients, lubricants, binders and disintegrating agents for solid preparations, and solvents, dissolution aids, suspending agents, isotonizing agents, buffers and soothing agents for liquid preparations. Other pharmaceutical additives such as preservatives, ant/oxidants, coloring agents and sweetening agents may be used as necessary. Preferable excipients include lactose, sucrose, D-mannitol, starch, crystalline cellulose and light silicic anhydride. Preferable lubricants include magnesium stearate, calcium stearate, talc and colloidal silica. Preferable binders include crystalline cellulose, sucrose, D-mannitol, dextrin, hydroxypropyl cellulose, hydroxypropylmethyl cellulose and polyvinylpyrrolidone. Preferable disintegrating agents include starch, carboxymethyl cellulose, carboxymethyl cellulose calcium, crosscarmellose sodium and carboxymethyl starch sodium. Preferable solvents include water for injection, alcohol, propylene glycol, macrogol, sesame oil and corn oil. Preferable dissolution aids include polyethylene glycol, propylene glycol, D-mannitol, benzyl benzoate, ethanol, tris-aminomethane, cholesterol, triethanolamine, sodium carbonate and sodium citrate.

Preferable suspending agents include surfactants such as stearyltriethanolamine, sodium lauryl sulfate, laurylaminopropionic acid, lecithin, benzalkonium chloride, benzethonium chloride and monostearic glycerol, and hydrophilic polymers such as polyvinyl alcohol, polyvinylpyrrolidone, carboxymethyl cellulose sodium, methyl cellulose, hydroxymethyl cellulose, hydroxyethyl cellulose and hydroxypropyl cellulose. Preferable isotonizing agents include sodium chloride, glycerol and D-mannitol Preferable buffers include buffer solutions of phosphates, acetates, carbonates and citrates. Preferable soothing agents include benzyl alcohol. Preferable preservatives include p-oxybenzoic acid esters, chlorobutanol, benzyl alcohol, phenethyl alcohol, dehydroacetic acid and sorbic acid. Preferable antioxidants include sulfites and ascorbic acid.

The present invention also provides a method of producing the compound (or salt thereof) represented by formula (I).

The compound (or salt thereof) represented by formula (I) can, for example, be produced as follows. The salts of compounds represented by formulae (II) and (III) below are exemplified by the same salts as specified for the compound represented by formula (I).

Method A

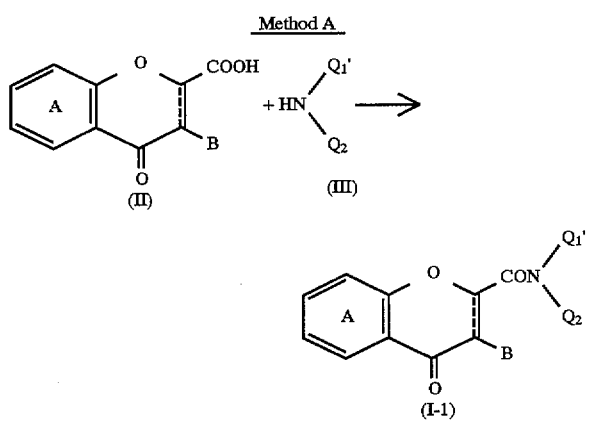

wherein the symbols have the same definitions as above.

In this method, compound (I-1) is produced by reacting compound (II) with phosphonic acid ester derivative (III).

Condensation of compounds (II) and (III) is carried out by an ordinary means of peptide synthesis. Any optionally chosen known method can be used for this peptide synthesis, including the methods described by M. Bodansky and M. A. Ondetti in Peptide Synthesis, Interscience Publishers, New York (1966), by F. M. Finn and K. Holmann in The Proteins, Vol. 2, edited by H. Nenrath and R. L. Hill, Academic Press Inc., New York (1976) and by Nobuo Izumiya et al. in Peputido Gosei No Kiso To Jikken (in Japanese), Maruzen (1985), specifically the azide method, chloride method, acid anhydride method, mixed acid anhydride method, DCC method, actived ester method, the method using Woodward reagent K, the carbonyldiimidazole method, oxidation reduction method, DCC/HONB method and the method using diethyl phosphorocyanidate (DEPC). This condensation reaction can be carried out in a solvent. The solvent is exemplified by anhydrous or hydrated N,N-dimethylformamide, dimethyl sulfoxide, pyridine, chloroform, dichloromethane, tetrahydrofuran, dioxane and acetonitrile and appropriate mixtures thereof. Reaction temperature is normally about −20° to 50° C., preferably −10° to 30° C. Reaction time is normally 1 to 100 hours, preferably 2 to 40 hours.

Benzopyran derivative (I-1) thus obtained may be isolated and purified by known means of separation and purification such as concentration, concentration under reduced pressure, solvent extraction, crystallization, recrystallization, redissolution and chromatography.

Method B

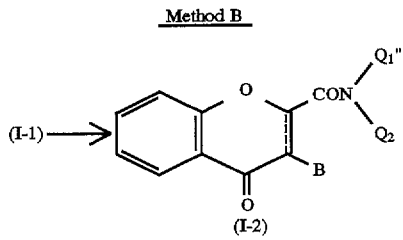

wherein $Q_1''$ represents a hydrocarbon residue which is substituted with the group represented by the formula, —X—P(O)(OH)$_2$, and the other symbols have the same definitions as above. The hydrocarbon residue for $Q_1''$ is exemplified by the same hydrocarbon residue as specified for $Q_1$ and $Q_1'$ above.

In this method, phosphonic acid ester derivative (I-1) as obtained by method A is hydrolyzed to corresponding phosphonic acid (I-2).

This reaction is carried out in a solvent which does not adversely affect the reaction, using an inorganic acid such as hydrochloric acid, hydrobromic acid or a halogenated trialkylsilane.

When using an inorganic acid such as hydrochloric acid or hydrobromic acid, an alcohol such as methanol, ethanol, 2-methoxyethanol, ethylene glycol, propanol or butanol, water or a mixed solvent thereof is used as a solvent. The amount of acid used is normally in substantial excess, the representative temperature being 0° to 150° C., preferably 30° to 100° C., reaction time being 1 to 50 hours.

When using a halogenated trialkylsilane such as chlorotrimethylsilane, bromotrimethylsilane or iodotrimethylsilane, a halogenated hydrocarbon such as carbon tetrachloride, chloroform, dichloromethane, 1,2-dichloroethane or 1,1,2,2-tetrachloroethane, acetonitrile or a mixed solvent thereof is used as a solvent.

The amount of halogenated trialkylsilane used is normally 1 to 10 equivalents, preferably 2 to 5 equivalents relative to the compound containing the mono- or di-alkoxyphosphoryl group. Reaction temperature is −30° to 100° C., preferably −10° to 50° C., reaction time being 30 minutes to 100 hours.

The thus-obtained phosphonic acid may be converted into a salt by ordinary treatment with a base such as potassium hydroxide, sodium hydroxide, sodium methoxide, ammonia or organic amine.

Phosphonic acid derivative (I-2) thus obtained may be isolated and purified by known means of separation and purification such as concentration, concentration under reduced pressure, solvent extraction, crystallization, recrystallization, redissolution and chromatography.

Method C

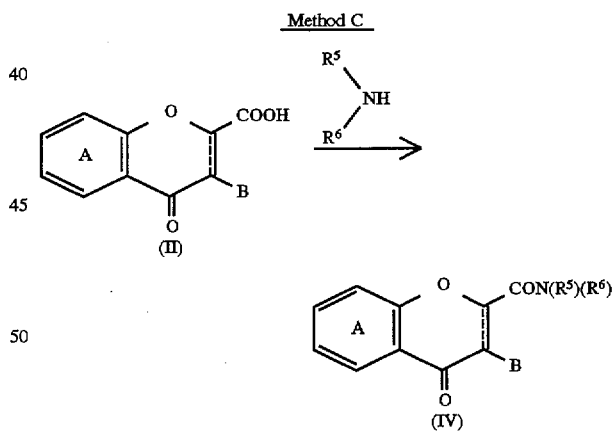

wherein the symbols have the same definitions as above.

In this method, benzopyran derivative (IV) and an amine derivative are reacted to produce compound (IV). This method is carried out in the manner as method A.

Benzopyran derivative (II), the starting material compound for methods A and C, can be produced by known methods such as those described in the overview of Progress in Medicinal Chemistry, Vol. 9, p. 65 (1973), and in Liebigs Annalen der Chemie, p. 1552 (1973). For example, benzopyran derivative (IV-1) is produced by method D.

Method D

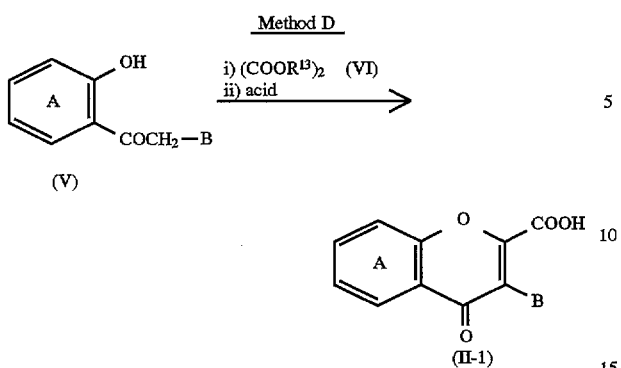

wherein $R^{13}$ represents a lower alkyl group; the other symbols have the same definitions as above.

The lower alkyl group for $R^{13}$ is exemplified by the same groups as specified for $R^3$ and $R^4$ above.

In this method, the compound represented by formula (V) is first reacted with oxalic acid ester (VI) in an appropriate solvent in the presence of a base (first stage reaction) and then treated with acid (second stage reaction) to synthesize compound (II-1).

The first stage reaction is carried out in a solvent in the presence of a base. The solvent is exemplified by aromatic hydrocarbons such as benzene, toluene and xylene, halogenated hydrocarbons such as chloroform, dichloromethane, 1,2-dichloroethane and 1,1,2,2-tetrachloroethane, ethers such as diethyl ether, tetrahydrofuran and dioxane, alcohols such as methanol, ethanol, propanol and 2-methoxyethanol, N,N-dimethylformamide, dimethyl sulfoxide and mixed solvents thereof. The base is exemplified by sodium alkoxides such as sodium methoxide and sodium ethoxide, potassium alkoxides such as potassium ethoxide and potassium tert-butoxide, sodium hydride, potassium hydride, sodium hydroxide and potassium hydroxide. The mount of oxalic acid ester (VI) used is normally 1 to 3 mol equivalents relative to compound (V), and that of base used is normally 1 to 10 mol equivalents, preferably 2 to 5 mol equivalents relative to compound (V). This reaction is carried out at –20° to 150° C., preferably 0° to 120° C for 0.5 to 10 hours.

The compound obtained in the first stage reaction is subjected to the second stage reaction to produce compound (II-1). The second stage reaction is carried out by heating in acetic acid, an ether such as diethyl ether, tetrahydrofuran or dioxane, an alcohol such as methanol, ethanol, propanol or 2-methoxyethanol, N,N-dimethylformamide, dimethyl sulfoxide, acetonitrile, 2-butanone, water or a mixed solvent thereof in the presence of an inorganic acid such as hydrochloric acid or sulfuric acid. The amount of inorganic acid used is normally in large excess, and the reaction is carried out at 20° to 180° C. for 0.5 to 30 hours.

Benzopyran derivative (II-1) thus obtained may be isolated and purified by known means of separation and purification such as concentration, concentration under reduced pressure, solvent extraction, crystallization, recrystallization, redissolution and chromatography.

Of the compounds represented by formula (III) above, compound (III-1), in which $R^3$ and $R^4$ have bound together to form a ring, can, for example, be produced by method E.

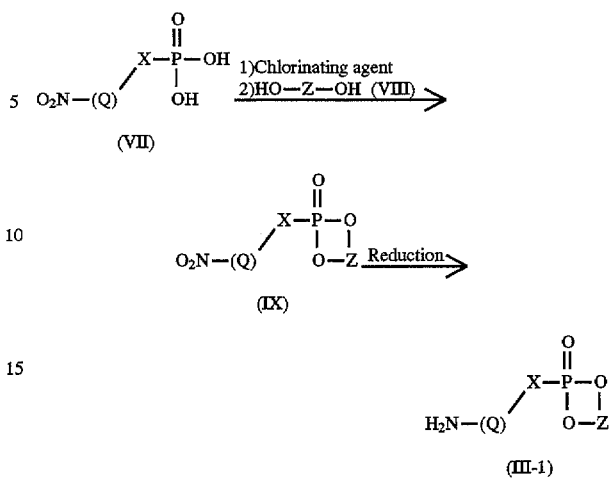

wherein (Q) is a hydrocarbon residue and the other symbols have the same definitions as above. The hydrocarbon residue for (Q) is exemplified by the same definition as specified for $Q_1$ and $Q_1'$ above.

In this method, the compound represented by general formula (VII) is first reacted with a chlorinating agent and then reacted with diol (VIII) to yield compound (IX), which is then reduced to compound (III-1).

Chlorination of compound (VIII) is carried out in an appropriate solvent or in the absence thereof. The solvent is exemplified by aromatic hydrocarbons such as benzene, toluene and xylene, ethers such as dioxane, tetrahydrofuran and dimethoxyethane, pyridine, chloroform, dichloromethane, 1,2-dichloroethane and 1,1,2,2-tetrachloroethane and mixed solvents thereof. The chlorinating agent is exemplified by thionyl chloride, oxalyl chloride, phosphorus oxychloride and phosphorus pentachloride, with preference given to thionyl chloride and oxalyl chloride. This reaction is advantageously carried out in the presence of a catalytic amount of N,N-dimethylformamide. Reaction temperature is normally -100 to 150° C., preferably –80° to 100° C. The amount of chlorinating agent used is normally 1 to 10 mol equivalents, preferably 1 to 5 mol equivalents relative to compound (VII). Reaction time is normally 0.5 to 10 hours. This reaction is followed by reaction with a diol (VIII) to produce compound (IX). This reaction is carried out in an appropriate solvent in the presence of a base. The solvent is exemplified by aromatic hydrocarbons such as benzene, toluene and xylene, ethers such as dioxane, tetrahydrofuran and dimethoxyethane, acetonitrile, chloroform, dichloromethane, 1,2-dichloroethane, 1,1,2,2-tetrachloroethane and mixed solvents thereof. Appropriate bases include alkali metal salts such as sodium hydroxide, potassium hydroxide, potassium carbonate, sodium carbonate and sodium hydrogen carbonate, amines such as pyridine, triethylamine and N,N-dimethylaniline, sodium hydride and potassium hydride. The mount of such base used is preferably about 1 to 5 mol equivalents relative to compound (VII), and the amount of diol used is preferably 1 to 5 mol equivalents relative to compound (VII). This reaction is carried out normally at –80° to 150° C., preferably –80° to 80° C. for 1 to 50 hours.

Reduction of compound (IX) can be carried out by known methods, including reduction with a metal hydride, reduction with a metal-hydrogen complex compound, reduction with diborane, and catalytic hydrogenation. Accordingly, this reaction is carried out by treating compound (IX) with a reducing agent. Reducing agents include metals and metal salts such as alkali metal borohydrides (e.g., sodium borohydride and lithium borohydride), metal-hydrogen complex compounds such as lithium aluminum hydride, metal hydroxides such as sodium hydride, organic tin compounds (e.g., triphenyltin hydride), nickel compounds and zinc compounds, catalytic reducing agents consisting of a transition metal such as palladium, platinum or rhodium and hydrogen, and diborane. The reaction is advantageously carried out by catalytic reduction using a combination of a transition metal such as palladium, platinum or rhodium and hydrogen. This reaction is carried out in an organic solvent which does not affect the reaction. The solvent is exemplified by aromatic hydrocarbons such as benzene, toluene and xylene, halogenated hydrocarbons such as chloroform, carbon tetrachloride, dichloromethane, 1,2-dichloroethane and 1,1,2,2-tetrachloroethane, ethers such as diethyl ether, tetrahydrofuran and dioxane, alcohols such as methanol, ethanol, propanol, isopropanol and 2-methoxyethanol, amides such as N,N-dimethylformamide and mixed solvents thereof, chosen as appropriate depending on type of reducing agent. Reaction temperature is normally $-20°$ to $150°$ C., preferably $0°$ to $100°$ C., reaction time being about 1 to 24 hours.

Compound (III-1) thus obtained may be isolated and purified by known means of separation and purification such as concentration, concentration under reduced pressure, solvent extraction, crystallization, recrystallization, redissolution and chromatography.

The compound (or salt thereof) represented by formulae (I) and (IV) can be used to prevent or treat various metabolic bone diseases, such as osteoporosis, in mammals (e.g., humans, mice, rats, cats, dogs, rabbits, bovines and swines) because it potently promotes osteogenesis. With low toxicity, the compound (or salt thereof) represented by formulae (I) and (IV) can be safely used. For example, when the compounds of Examples 4 and 10 were orally administered to mice at a dose of each 300 mg/kg, no deaths occurred.

When used as a prophylactic/therapeutic agent for osteoporosis, for instance, the compound (or salt thereof) represented by formulae (I) and (IV) is administered at a daily dose of 5 to 1,000 mg, preferably 10 to 600 mg, as the active ingredient, depending on patient condition and weight and method of administration, for each adult (weighing 50 kg), in 1 to 3 portions per day, in the case of oral administration.

The present invention is hereinafter described in more detail by means of the following test example, reference examples and working examples, which examples, however, do not by any means limit the invention.

TEST EXAMPLE

Osteogenesis-stimulating action

Using stromal cells prepared from the femoral marrow of a normal rat, alkaline phosphatase activity was determined as an index of osteogenesis. Specifically, stromal cells, prepared from the femoral marrow of a 7-week-old male Sprague-Dawley rat by the method of Maniatopoulos et al. [Cell Tissue Research, Vol. 254, p. 317 (1988)], were cultured in an α-MEM (minimum essential medium) solution containing both dexamethasone ($10^{-7}$M) and β-glycerophosphoric acid ($10^{-2}$M) to obtain calcified bone-like tissue. One week later, the test compound ($10^{-7}$M or $10^{-5}$M) was added to the confluent cells, followed by 10 to 14 more days of culture in the above culture medium. After washing with phosphate buffer, the cells were homogenized with 0.2% Nonidet P-40 and centrifuged at 3,000 rpm for 10 minutes. The resulting supernatant was assayed for alkaline phosphatase activity by the method of Lowry et al. [Journal of Biological Chemistry, Vol. 207, p. 19 (1954)]. The values obtained are given in mean±SE in Table 1. The data were statistically analyzed by Student's t-test.

TABLE 1

| Compound | Concentration (M) | Alkaline Phosphatase Activity (nmol p-nitrophenol/min/well) |
| --- | --- | --- |
| Control | Not added | 139.5 ± 9.5 |
| Compound obtained in Example 2 | $10^{-5}$ | 258.0 ± 37.5* |
| Compound obtained in Example 1 | $10^{-5}$ | 823.8 ± 53.1* |
| Control | Not added | 138.0 ± 4.3 |
| Compound obtained in Example 4 | $10^{-5}$ | 311.4 ± 35.3* |
| Compound obtained in Example 10 | $10^{-5}$ | 309.6 ± 41.1* |
| Control | Not added | 413.0 ± 23.6 |
| Compound obtained in Example 25 | $10^{-5}$ | 2,088.0 ± 145.0* |
| Compound obtained in Example 34 | $10^{-5}$ | 1,054.8 ± 99.0* |
| Control | Not added | 545.9 ± 31.8 |
| Compound obtained in Example 21 | $10^{-5}$ | 2,473.2 ± 111.2* |

*$p < 0.01$ vs control

From Table 1, it is seen that the benzopyran derivatives relating to the present invention, represented by formulae (I) and (IV), show excellent osteoblast activating action and are useful as prophylactic/therapeutic drugs for metabolic bone diseases, including osteoporosis. Furthermore, these compounds showing stimulatory effects on bone formation can be expected to be useful in healing bone defects in humans such as bone fracture, osteoarthritis and so on in the field of orthopaedic surgery. In addition, they will be applicable to repair of broken periodontal tissue in periodontal disease, stabilization of artificial tooth root, formation of maxillary bones and repair of cleft palate in the dental field.

REFERENCE EXAMPLE 1

2'-hydroxyacetophenone (25.7 g) and diethyl oxalate (33.1 g) were added to a solution of sodium ethoxide in ethanol (prepared from 13.0 g of sodium and 375 ml of ethanol), and the mixture was heated for 1 hour while refluxing. After the reaction mixture was cooled to room temperature, ethyl ether (500 ml) was added, and the separating crystals were collected by filtration. To this crystal, 2N hydrochloric acid (600 ml) was added, followed by ethyl ether extraction. The ethyl ether layer was washed with water and dried (MgSO$_4$), after which it was concentrated under reduced pressure. The residual oily substance was dissolved in acetic acid-concentrated hydrochloric acid (1:1, 200 ml) and heated for 1 hour while refluxing. The reaction mixture was poured over water (1 liter); the separated crystals were collected by filtration and then washed by sequential additions of water, ethanol and ethyl ether in that order, to yield 4-oxo-4H-1-benzopyran-2-carboxylic acid (83.5%), which was then recrystallized from ethanol to yield colorless needles having a melting point of 240° to 241° C. (decomposed).

REFERENCE EXAMPLES 2 THROUGH 5

The compounds listed in Table 2 were obtained in the same manner as in Reference Example 1.

TABLE 2

A¹ at position 8, A² at position 5 on benzopyran-4-one-2-carboxylic acid structure (positions 5,6,7,8 on benzene ring fused to pyranone with COOH at 2-position and =O at 4-position).

| Reference Example No. | A¹, A² | Yield (%) | Melting Point (°C.) | Recrystallizing Solvent |
|---|---|---|---|---|
| 2 | 6,7-(CH₃)₂ | 70 | 256–257 | Ethanol-isopropyl ether |
| 3 | 6,7-(OCH₂O) | 70 | 245–246 | N,N-dimethylformamide-water |
| 4 | 6,7-(CH₃O)₂ | 63 | 285–287 | N,N-dimethylformamide-water |
| 5 | 6-Cl, H | 45 | 236–237 | Ethanol-hexane |
| 6 | 6-(CH₃)₂CH, H | 37 | 194–195 | Ethyl acetate-hexane |

REFERENCE EXAMPLE 7

A mixture of phenol (22.41 g), sodium (5.47 g) and toluene (500 ml) was heated for 4 hours while refluxing. The reaction mixture was cooled to 85° C., and maleic anhydride (23.35 g) was added. After stirring at 85° C. for 1 hour, the reaction mixture was poured over ice-water, and the aqueous layer was collected. The aqueous layer was acidified with concentrated hydrochloric acid and extracted with ethyl acetate. The ethyl acetate layer was washed with water, dried (MgSO₄) and then treated with activated charcoal, after which the solvent was distilled off, to yield fumaric acid monophenyl ester (10.59 g, 23%), which was then recrystallized from ethyl acetate-hexane to yield colorless needles having a melting point of 127° to 128° C.

REFERENCE EXAMPLE 8

A mixture of fumaric acid monophenyl ester (10.19 g), powdered anhydrous aluminum chloride (21.21 g) and sodium chloride (6.20 g) was heated at 180° C. for 30 minutes. After cooling, the reaction mixture was treated with 1N HCl (300 ml) and extracted with ethyl acetate. The ethyl acetate layer was washed with water, dried (MgSO₄) and then treated with activated charcoal, after which the solvent was distilled off, to yield 3-(2-hydroxybenzoyl)acrylic acid (3.37 g, 33%), which was then recrystallized from ethanol-hexane to yield yellow prisms having a melting point of 172° to 173° C.

REFERENCE EXAMPLE 9

A solution of 3-(2-hydroxybenzoyl)acrylic acid (3.02 g) in aqueous sodium carbonate (5%, 55 ml) was stirred at room temperature for 15 hours, acidified with 2N HCl and extracted with ethyl acetate. The ethyl acetate layer was washed with water, dried (MgSO₄) and then treated with activated charcoal, after which the solvent was distilled off, to yield 2,3-dihydro-4-oxo-4H-1-benzopyran-2-carboxylic acid (2.01 g, 67%), which was then recrystallized from ethyl acetate-hexane to yield colorless prisms having a melting point of 170° to 171° C.

REFERENCE EXAMPLE 10

2'-Hydroxypropiophenone (15.02 g) and diethyl oxalate (17.54 g) were added to a solution of sodium ethoxide in ethanol (prepared from 6.90 g of sodium and 200 ml of ethanol), and the mixture was heated for 2.5 hours while refluxing. The mixture was cooled, poured over 2N HCl (320 ml) and extracted with ethyl acetate. The ethyl acetate layer was washed with water and dried (MgSO₄), after which the solvent was distilled off. The residue was subjected to silica gel column chromatography and eluted with ethyl acetate-hexane (1:3, v/v) to yield an oily substance (4.26 g). This oily substance was dissolved in acetic acid-concentrated hydrochloric acid (1:1, 30 ml) and heated for 1 hour while refluxing. After cooling, the reaction mixture was poured over water (150 ml) and stirred at room temperature for 10 minutes. The separated crystals were collected by filtration to yield 3-methyl-4-oxo-4H-1-benzopyran-2-carboxylic acid (2.62 g, 13%), which was then recrystallized from ethanol to yield colorless prisms having a melting point of 192° to 193° C.

REFERENCE EXAMPLE 11

A mixture of 4-nitrobenzylphosphonic acid (37.40 g), thionyl chloride (150 ml) and N,N-dimethylformamide (5 drops) was heated for 5 hours while refluxing, after which it was concentrated under reduced pressure. The residue was dissolved in tetrahydrofuran (500 ml), and a solution of ethylene glycol (10.69 g) in acetonitrile (90 ml) was added dropwise at −78° C. over a 15 minute period. Next, pyridine (28.61 g) was added dropwise at −78° C. over a 15-minute period, and the mixture was stirred at room temperature for 15 hours. After the insoluble solid was filtered off, the filtrate was concentrated under reduced pressure, and the residue was dissolved in chloroform (400 ml). The insoluble solid, previously filtered off, was added to water (800 ml)chloroform (200 ml), and the chloroform layer was collected. The chloroform layer was combined and then washed by sequential additions of 1N HCl, water, a saturated aqueous solution of sodium hydrogen carbonate and water in that order, dried (MgSO₄) and then treated with activated charcoal, after which the solvent was distilled off, to yield 2-(4-nitrobenzyl)-1,3,2-dioxaphospholane-2-oxide (8.86 g, 21%), which was then recrystallized from ethanol-hexane to yield colorless plates having a melting point of 144° to 145° C.

REFERENCE EXAMPLE 12

Oxalyl chloride (22.09 g) was added dropwise to a mixture of 4-nitrobenzylphosphonic acid (17.99 g), pyridine (13.76 g) and tetrahydrofuran (500 ml) at −78° C. After the mixture was stirred at −78° C. for 30 minutes and then at room temperature for 1.5 hours, the insoluble solid was filtered off. The filtrate was concentrated under reduced pressure, and the residual oily substance was dissolved in tetrahydrofuran (500 ml). To this solution, a solution of 1,3-propanediol (2.58 g) in acetonitrile (30 ml) was added dropwise at −78° C. over a 15-minute period. Then, pyridine (5.62 g) was added dropwise at −78° C. over a 5-minute period, and the mixture was stirred at room temperature for 15 hours. After the insoluble solid was filtered off, the filtrate was concentrated under reduced pressure. The residue was subjected to silica gel column chromatography and eluted with ethyl acetate-chloroform-methanol (10:10:1, v/v) to yield 2-(4-nitrobenzyl)-1,3,2-dioxaphosphorinane-2-oxide (5.62 g, 26%), which was then recrystallized from ethanol-hexane to yield colorless needles having a melting point of 144° to 145° C.

REFERENCE EXAMPLE 13

With 4-nitrobenzylphosphonic acid and 2,2-dimethyl-1,3-propanediol, the same procedure as in Reference Example 11 was followed, to yield 5,5-dimethyl-2-(4-nitrobenzyl)-1, 3,2-dioxaphosphorinane-2-oxide, which was then recrystallized from ethanol-hexane to yield colorless plates having a melting point of 176° to 177° C.

REFERENCE EXAMPLE 14

With 4-nitrobenzylphosphonic acid and 2,4-pentanediol, the same procedure as in Reference Example 11 was followed, to yield 4,6-dimethyl-2-(4-nitrobenzyl)-1,3,2-dioxaphosphorinane-2-oxide, which was then recrystallized from ethanol-hexane to yield colorless needles having a melting point of 152° to 153° C.

REFERENCE EXAMPLE 15

With 4-nitrobenzylphosphonic acid and 1,4-butanediol, the same procedure as in Reference Example 11 was followed, to yield 2-(4-nitrobenzyl)-1,3,2-dioxaphosphepane-2-oxide, which was then recrystallized from ethanol-hexane to yield colorless needles having a melting point of 136° to 137° C.

REFERENCE EXAMPLE 16

A mixture of 2-(4-nitrobenzyl)-1,3,2-dioxaphospholane-2-oxide (8.56 g), palladium-carbon (5%, 50% wet, 4.0 g) and methanol (300 ml) was subjected to a catalytic hydrogenation at room temperature and under 1 atm. After the catalyst was filtered off, the filtrate was concentrated under reduced pressure to yield 2-(4-aminobenzyl)-1,3,2-dioxaphospholane-2-oxide (4.25 g, 57%), which was then recrystallized from ethanol-hexane to yield colorless prisms having a melting point of 183° to 184° C.

REFERENCE EXAMPLE 17

2-(4-Nitrobenzyl)-1,3,2-dioxaphosphorinane-2-oxide was subjected to a catalytic hydrogenation in the same manner as in Reference Example 16 to yield 2-(4-aminobenzyl)-1,3,2-dioxaphosphorinane-2-oxide, which was then recrystallized from ethanol-hexane to yield colorless needles having a melting point of 172° to 173° C.

REFERENCE EXAMPLE 18

5,5-Dimethyl-2-(4-nitrobenzyl)-1,3,2-dioxaphosphorinane-2-oxide was subjected to a catalytic hydrogenation in the same manner as in Reference Example 16 to yield 2-(4-aminobenzyl)-5,5-dimethyl-1,3,2-dioxaphosphorinane-2-oxide, which was then recrystallized from ethanol-hexane to yield colorless needles having a melting point of 152° to 153° C.

REFERENCE EXAMPLE 19

4,6-Dimethyl-2-(4-nitrobenzyl)-1,3,2-dioxaphosphorinane-2-oxide was subjected to a catalytic hydrogenation in the same manner as in Reference Example 16 to yield 2-(4-aminobenzyl)-4,6-dimethyl-1,3,2-dioxaphosphorinane-2-oxide, which was then recrystallized from ethanol-hexane to yield colorless prisms having a melting point of 160° to 161° C.

REFERENCE EXAMPLE 20

2-(4-Nitrobenzyl)-1,3,2-dioxaphosphepane-2-oxide was subjected to a catalytic hydrogenation in the same manner as in Reference Example 16 to yield 2-(4-aminobenzyl)-1,3,2-dioxaphosphepane-2-oxide, which was then recrystallized from ethanol-hexane to yield colorless prisms having a melting point of 128° to 129° C.

REFERENCE EXAMPLE 21

With 4-nitrobenzylphosphonic acid and 2-methyl-1,3-propanediol, the same procedure as in Reference Example 11 was followed, to yield 5-methyl-2-(4-nitrobenzyl)-1,3,2-dioxaphosphorinane-2-oxide, which was then recrystallized from ethanol-hexane to yield colorless prisms having a melting point of 170° to 171° C.

REFERENCE EXAMPLE 22

With 4-nitrobenzylphosphonic acid and 2-ethyl-2-methyl-1,3-propanediol, the same procedure as in Reference Example 11 was followed, to yield 5-ethyl-5-methyl-2-(4-nitrobenzyl)-1,3,2-dioxaphosphorinane-2-oxide, which was then recrystallized from ethanol-hexane to yield colorless prisms having a melting point of 184° to 185° C.

REFERENCE EXAMPLE 23

With 4-nitrobenzylphosphonic acid and 2,2-diethyl-1,3-propanediol, the same procedure as in Reference Example 11 was followed, to yield diethyl-2-(4-nitrobenzyl)-1,3,2-dioxaphosphorinane-2-oxide, which was then recrystallized from ethanol-hexane to yield colorless prisms having a melting point of 159° to 160° C.

REFERENCE EXAMPLE 24

With 4-nitrobenzylphosphonic acid and 2-butyl-2-ethyl-1,3-propanediol, the same procedure as in Reference Example 11 was followed, to yield 5-butyl-5-ethyl-2-(4-nitrobenzyl)-1,3,2-dioxaphosphorinane-2-oxide, which was then recrystallized from ethanol-hexane to yield colorless prisms having a melting point of 111° to 112° C.

REFERENCE EXAMPLE 25

5-Methyl-2-(4-nitrobenzyl)-1,3,2-dioxaphosphorinane-2-oxide was subjected to a catalytic hydrogenation in the same manner as in Reference Example 16 to yield 2-(4-aminobenzyl)-5-methyl-1,3,2-dioxaphosphorinane-2-oxide, which was then recrystallized from ethanol-hexane to yield colorless needles having a melting point of 158° to 159° C.

REFERENCE EXAMPLE 26

5-Ethyl-5-methyl-2-(4-nitrobenzyl)-1,3,2-dioxaphosphorinane-2-oxide was subjected to a catalytic hydrogenation in the same manner as in Reference Example 16 to yield 2-(4-aminobenzyl)-5-ethyl-5-methyl-1,3,2-dioxaphosphorinane-2-oxide, which was then recrystallized from ethanol-hexane to yield colorless needles having a melting point of 130° to 131° C.

REFERENCE EXAMPLE 27

5,5-Diethyl-2-(4-nitrobenzyl)-1,3,2-dioxaphosphorinane-2-oxide was subjected to a catalytic hydrogenation in the same manner as in Reference Example 16 to yield 2-(4-aminobenzyl)-5,5-diethyl-1,3,2-dioxaphosphorinane-2-oxide, which was then recrystallized from ethanol-hexane to yield colorless prisms having a melting point of 128° to 129° C.

REFERENCE EXAMPLE 28

5-Butyl-5-ethyl-2-(4-nitrobenzyl)-1,3,2-dioxaphosphorinane-2-oxide was subjected to a catalytic hydrogenation in the same manner as in Reference Example 16 to yield 2-(4-aminobenzyl)-5-butyl-5-ethyl-1,3,2- dioxaphosphorinane-2-oxide, which was then recrystallized from ethanol-hexane to yield colorless prisms having a melting point of 90° to 91° C.

REFERENCE EXAMPLE 29

Dimethyl 4-aminobenzylphosphonate (21.5 g) and then paraformaldehyde (80%, 5.3 g) were added at room temperature to a solution of sodium methoxide in methanol (prepared from 27 g of sodium and 250 ml of methanol). After this mixture was stirred at room temperature for 15 hours, sodium borohydride (3.8 g) was added, and the mixture was heated for 1.5 hours while refluxing. The reaction mixture was concentrated under reduced pressure and then the residue was treated with 1NKOH (500 ml) and extracted with chloroform. The chloroform layer was washed with water and dried (MgSO$_4$), after which the solvent was distilled off. The residue was subjected to silica gel column chromatography and eluted with ethyl acetate-chloroform-methanol (25:25:1, v/v) to yield dimethyl 4-methylaminobenzylphosphonate (2.9 g, 13%) as an oily subsatance. NMR($\delta$ ppm in CDCl$_3$): 2.55(1H,broad s), 2.82 (3H,s), 3.07(2H,d,J=21 Hz), 3.63(3H,s), 3.69(3H,s), 6.57 (2H,dd,J=9&1 Hz), 7.11(2H,dd,J=9&3 Hz)

EXAMPLE 1

Oxalyl chloride (2.28 g) and then N,N-dimethylformamide (1 drop) were added at 0° C. to a solution of 4-oxo-4H-1-benzopyran-2-carboxylic acid (2.85 g) in tetrahydrofuran (60 ml). After stirring at room temperature for 2.5 hours, this mixture was concentrated under reduced pressure. The residue was dissolved in tetrahydrofuran (25 ml), and this solution was added dropwise to a solution of diethyl 4-aminobenzylphosphonate (4.01 g) and triethylamine (1.67 g) in tetrahydrofuran (90 ml) at room temperature. After stirring at room temperature for 1 hour, the reaction mixture was poured over water and extracted with chloroform. The chloroform layer was washed with water and dried (MgSO$_4$), after which the solvent was distilled off, to yield N-(4-diethoxyphosphorylmethylphenyl)-4-oxo-4H-1-benzopyran-2-carboxamide. (4.79 g, 76.9%), which was then recrystallized from ethanol-isopropyl ether to yield yellow plates having a melting point of 153° to 154° C.

EXAMPLES 2 THROUGH 8

The compounds listed in Table 3 were obtained in the same manner as in Example 1.

TABLE 3

| Example No. | A$^1$, A$^2$ | W | Yield (%) | Melting Point (°C.) | Recrystallizing Solvent |
|---|---|---|---|---|---|
| 2 | H, H | —C$_6$H$_4$—P(O)(OC$_2$H$_5$)$_2$ | 59 | 162–163 | Ethanol-isopropyl ether |
| 3 | 6,7-(CH$_3$)$_2$ | —C$_6$H$_4$—P(O)(OC$_2$H$_5$)$_2$ | 60 | 258–259 | Methanol |
| 4 | 6,7-(CH$_3$)$_2$ | —C$_6$H$_4$—CH$_2$P(O)(OC$_2$H$_5$)$_2$ | 67 | 189–190 | Ethanol-isopropyl ether |
| 5 | 6,7-(OCH$_2$O) | —C$_6$H$_4$—CH$_2$P(O)(OC$_2$H$_5$)$_2$ | 64 | 204–205 | Ethanol |
| 6 | 6,7-(CH$_3$O)$_2$ | —C$_6$H$_4$—CH$_2$P(O)(OC$_2$H$_5$)$_2$ | 22 | 215–216 | Chloroform-ethanol |
| 7 | 6-Cl, H | —C$_6$H$_4$—CH$_2$P(O)(OC$_2$H$_5$)$_2$ | 66 | 203–204 | Ethanol |

TABLE 3-continued

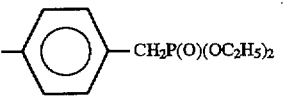

| Example No. | $A^1$, $A^2$ | W | Yield (%) | Melting Point (°C.) | Recrystallizing Solvent |
|---|---|---|---|---|---|
| 8 | 6-$(CH_3)_2$CH, H | —⟨phenyl⟩—$CH_2P(O)(OC_2H_5)_2$ | 56 | 129–130 | Ethyl acetate-hexane |

EXAMPLES 9 THROUGH 16

The compounds listed in Table 4 were obtained in the same manner as in Example 1.

TABLE 4

| Example No. | $A^1$, $A^2$ | W | Yield (%) | Melting Point (°C.) | Recrystallizing Solvent |
|---|---|---|---|---|---|
| 9 | H, H | 4-Cl-phenyl | 86 | 257–258 | N,N-dimethylformamide-water |
| 10 | H, H | 3-pyridyl | 70 | 220–221 | Ethanol |
| 11 | 6,7-$(CH_3)_2$ | 4-Cl-phenyl | 67 | >300 | N,N-dimethylformamide-water |
| 12 | 6,7-$(CH_3)_2$ | 3-pyridyl | 64 | 291–292 | N,N-dimethylformamide-water |
| 13 | 6,7-$(OCH_2O)$ | 2-methyl-5-styryl-thiazolyl | 31 | 288–289 | N,N-dimethylformamide-water |
| 14 | 6,7-$(CH_3O)_2$ | 2-methyl-5-styryl-thiazolyl | 17 | 215–216 | Chloroform-ethyl acetate |

TABLE 4-continued

[Structure: benzopyran-2-carboxamide with A¹ at position 8, A² at position 5, CONH—W at position 2]

| Example No. | A¹, A² | W | Yield (%) | Melting Point (°C.) | Recrystallizing Solvent |
|---|---|---|---|---|---|
| 15 | 6-Cl, H | [thiazole-styryl structure] | 53 | 300–301 | N,N-dimethylformamide-water |
| 16 | 6-(CH₃)₂CH, H | [thiazole-styryl structure] | 40 | 222–223 | Chloroform-ethanol |

EXAMPLE 17

Iodotrimethylsilane [(CH₃)₃SiI] (3.17 g) was added at 0° C. to a mixture of N-(4-diethoxyphosphorylmethylphenyl)-4-oxo-4H-1-benzopyran-2-carboxamide (2.99 g) and carbon tetrachloride (60 ml). This mixture was stirred at 0° C. for 1 hour and then at room temperature for 15 hours, after which it was concentrated under reduced pressure. The residue was dissolved in methanol (45 ml), poured over 4N HCl and stirred at room temperature for minutes. The separated crystals were collected by filtration and recrystallized from methanol to yield N-(4-phosphonomethylphenyl)-4-oxo-4H-1-benzopyran-2-carboxamide (0.22 g, 8.5%) as light yellow prisms having a melting point of 265° to 266° C.

EXAMPLES 18 THROUGH 34

The compounds listed in Table 5 were obtained in the same manner as in Example 1.

TABLE 5

[Structure: benzopyran with CONH—W at position 2 and B substituent at position 3]

| Example No. | B | W | Yield (%) | Melting Point (°C.) | Recrystallizing Solvent |
|---|---|---|---|---|---|
| 18 | H | 2-CH₃-C₆H₄—CH₂P(O)(OC₂H₅)₂ | 74 | 159–160 | Ethanol-hexane |
| 19 | H | 3-CH₃-C₆H₄—CH₂P(O)(OC₂H₅)₂ | 67 | 129–130 | Ethanol-hexane |
| 20 | H | 4-CH₃-C₆H₄—CH₂CH₂P(O)(OC₂H₅)₂ | 76 | 162–163 | Ethanol-hexane |
| 21 | H | 4-CH₃-C₆H₄—CH₂P(O)(OCH₃)₂ | 78 | 197–198 | Ethanol-hexane |

TABLE 5-continued

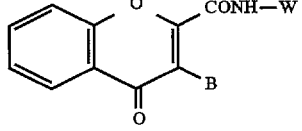

| Example No. | B | W | Yield (%) | Melting Point (°C.) | Recrystallizing Solvent |
|---|---|---|---|---|---|
| 22 | H | 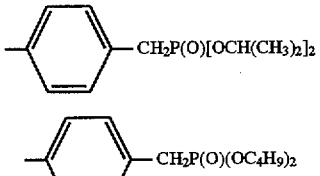 | 77 | 166–167 | Ethanol-hexane |
| 23 | H | 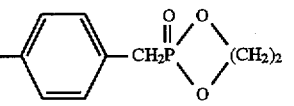 | 41 | 105–106 | Ethanol-hexane |
| 24 | H | 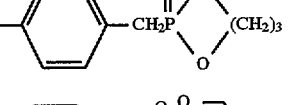 | 39 | 239–240 | Chloroform-ethanol |
| 25 | H | 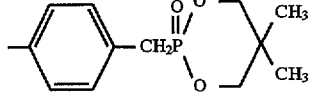 | 38 | 240–241 | Ethanol-hexane |
| 26 | H | 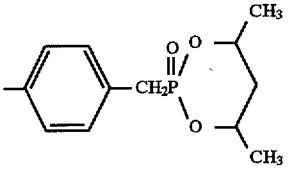 | 73 | 260–261 | Chloroform-ethanol |
| 27 | H | 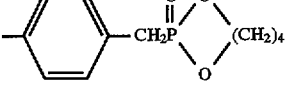 | 73 | 225–226 | Chloroform-ethnaol |
| 28 | H | 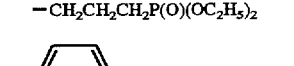 | 73 | 216–217 | Ethanol-hexane |
| 29 | H | —$CH_2CH_2P(O)(OCH_2H_5)_2$ | 73 | 115–116 | Ethyl acetate-hexane |
| 30 | H | —$CH_2CH_2CH_2P(O)(OC_2H_5)_2$ | 53 | 64–65 | Isopropyl ether |
| 31 | $CH_3$ | 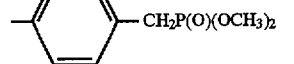 | 82 | 159–160 | Ethanol-hexane |
| 32 | $CH_3$ |  | 78 | 150–151 | Ethanol-hexane |
| 33 | $CH_3$ | 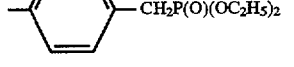 | 55 | 222–223 | Chloroform-ethanol |
| 34 | $CH_3$ | 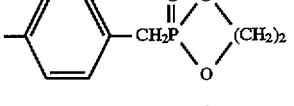 | 67 | 204–205 | Ethanol |

EXAMPLES 35 THROUGH 37

The compounds listed in Table 6 were obtained in the same manner as in Example 1.

TABLE 6

[Structure: benzopyran-4-one with CONH—W substituent at 2-position]

| Example No. | W | Yield (%) | Melting Point (°C.) | Recrystallizing Solvent |
|---|---|---|---|---|
| 35 | —⟨phenyl⟩—CH$_2$P(O)(OCH$_3$)$_2$ | 63 | 160–161 | Ethanol-hexane |
| 36 | —⟨phenyl⟩—CH$_2$P(O)(OC$_2$H$_5$)$_2$ | 61 | 156–157 | Ethanol-hexane |
| 37 | —⟨phenyl⟩—CH$_2$P(O)(O)(O)(CH$_2$)$_3$ (cyclic) | 29 | 201–202 | Ethanol-hexane |

EXAMPLE 38

Oxalyl chloride (0.97 g) and then N,N-dimethylformamide (1 drop) were added at 0° C. to a solution of 4-oxo-4H-1-benzopyran-2-carboxylic acid (1.22 g) in tetrahydrofuran (35 ml). After stirring at room temperature for 2 hours, this mixture was concentrated under reduced pressure. The residue was dissolved in tetrahydrofuran (15 ml), and an aqueous solution of methylamine (30%, 15 ml) was added at 0° C. After stirring at 0° C. for 1 hour, the reaction mixture was poured over water and extracted with chloroform. The chloroform layer was washed with water and dried (MgSO$_4$), after which the solvent was distilled off. The residue was subjected to silica gel column chromatography and eluted with ethyl acetate-chloroform (1:1, v/v) to yield crystals, which were then recrystallized from ethanol-hexane to yield N-methyl-4-oxo-4H-1-benzopyran-2-carboxamide (0.14 g, 11%) as colorless needles having a melting point of 224° to 225° C.

EXAMPLE 39

Oxalyl chloride (1.07 g) and then N,N-dimethylformamide (1 drop) were added at 0° C. to a solution of 4-oxo-4H-1-benzopyran-2-carboxylic acid (1.33 g) in tetrahydrofuran (35 ml). After stirring at room temperature for 2.5 hours, this mixture was concentrated under reduced pressure. The residual 4-oxo-4H-1-benzopyrane-2-carboxylic acid chloride was dissolved in tetrahydrofuran (15 ml). Separately, to a solution of diethyl phosphoramidte [H$_2$NP(O)(OC$_2$H$_5$)$_2$] (4.29 g) in tetrahydrofuran (70 ml), oily sodium hydride (60%, 0.56 g) was added at 0° C., followed by stirring at constant temperature for 30 minutes. To this mixture, the previously prepared solution of 4-oxo-4H-1-benzopyran-2-carboxylic acid chloride in tetrahydrofuran was added at 0° C. After stirring at 0° C. for 1 hour, the reaction mixture was poured over water and extracted with chloroform. The chloroform layer was washed with water and dried (MgSO$_4$), after which the solvent was distilled off. The residue was subjected to silica gel column chromatography and eluted with ethyl acetate-chloroform-methanol (15:15:1, v/v) to yield crystals, which were then recrystallized from ethanol-hexane to yield N-diethoxyphosphoryl-4-oxo-4H-1-benzopyran-2-carboxamide (0.72 g, 32%) as colorless needles having a melting point of 182° to 183° C.

EXAMPLES 40 THROUGH 47

The compounds listed in Table 7 were obtained in the same manner as in Example 1.

TABLE 7

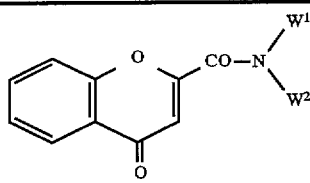

| Example No. | W¹ | W² | Yield (%) | Melting Point (°C.) | Recrystallizing Solvent |
|---|---|---|---|---|---|
| 41 | H | -C₆H₄-CH₂P(O)(O-)(O-)CH₃ (cyclic) | 57 | 256–257 | Chloroform-ethanol |
| 42 | H | -C₆H₄-CH₂P(O)(O-)(O-)C(CH₃)(C₂H₅) (cyclic) | 78 | 213–214 | Ethanol-hexane |
| 43 | H | -C₆H₄-CH₂P(O)(O-)(O-)C(C₂H₅)(C₂H₅) (cyclic) | 77 | 213–214 | Ethanol-hexane |
| 44 | H | -C₆H₄-CH₂P(O)(O-)(O-)C(C₂H₅)(C₄H₉) (cyclic) | 76 | 192–193 | Ethanol-hexane |
| 45 | CH₃ | -C₆H₄-CH₂P(O)(OCH₃)₂ | 80 | 142–143 | Ethanol-hexane |
| 46 | H | -C₆H₄-CH=C(P(O)(OC₂H₅)₂)₂ | 52 | 160–161 | Ethanol-hexane |
| 47 | H | -C₆H₄-CH₂CH(COOC₂H₅)(P(O)(OC₂H₅)₂) | 46 | 97–98 | Ethyl acetate-hexane |

PREPARATION EXAMPLES

A prophylactic or therapeutic drug for osteoporosis containing the compound (or salt thereof) represented by formula (I) or (IV) as an active ingredient can, for example, be produced with the following formulations:

1. Capsules

| | |
|---|---|
| (1) Compound obtained in Example 1 | 10 mg |
| (2) Lactose | 90 mg |
| (3) Microcrystalline cellulose | 70 mg |
| (4) Magnesium stearate | 10 mg |
| | Total 180 mg per capsule |

Components (1), (2) and (3) and a half portion of component (4) were mixed and granulated. To these granules, the remaining portion of component (4) was added, and the whole mixture was packed in a gelatin capsule.

2. Tablets

| | |
|---|---|
| (1) Compound obtained in Example 4 | 10 mg |
| (2) Lactose | 35 mg |
| (3) Corn starch | 150 mg |
| (4) Microcrystalline cellulose | 30 mg |
| (5) Magnesium stearate | 5 mg |
| | Total 230 mg per tablet |

Components (1), (2) and (3), a two-thirds portion of component (4) and a half portion of component (5) were mixed and granulated. To these granules, the remaining portions of components (4) and (5) were added, and the whole mixture was tableted by compressive tableting.

| | |
|---|---|
| (1) Hydrochloride of the compound obtained in Example 10 | 10 mg |
| (2) Inositol | 100 mg |
| (3) Benzyl alcohol | 20 mg |
| | Total 130 mg per ampule |

Components (1), (2) and (3) were dissolved in distilled water for injection to a final quantity of 2 ml, and the solution was packed in an ampule. The entire procedure was performed aseptically.

| 4. Capsules | |
|---|---|
| (1) Compound obtained in Example 21 | 10 mg |
| (2) Lactose | 90 mg |
| (3) Microcrystalline cellulose | 70 mg |
| (4) Magnesium stearate | 10 mg |
| | Total 180 mg per capsule |

Components (1), (2) and (3) and a half portion of component (4) were mixed and granulated. To these granules, the remaining portion of component (4) was added, and the whole mixture was packed in a gelatin capsule.

What is claimed is:

1. A method for the prophylaxis or treatment of metabolic bone diseases in a mammal comprising the step of administering a pharmaceutically effective amount of a compound represented by the formula:

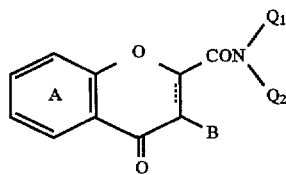

wherein B represents a hydrogen atom or a lower alkyl group; ring A represents a benzene ring which may have one or more substituents; ̄ represents a single or double bond; $Q_1$ represents the group represented by the formula,

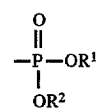

, or a hydrocarbon residue substituted with the group represented by the formula,

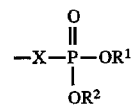

wherein X represents a bond or a spacer having a chain length of 1 to 4 atoms as the linear moiety which may have one or more side chains; $R^1$ and $R^2$, whether identical or not, independently represent a hydrogen atom or a lower alkyl, or may bind together to form a ring; $Q_2$ represents a hydrogen atom, a hydrocarbon residue which may be substituted or a heterocyclic ring residue which may be substituted; or a salt thereof, to a mammal in need thereof.

2. The method of claim 1, wherein the hydrocarbon residue for $Q_1$ is an aryl group.

3. The method of claim 2, wherein the aryl group is phenyl.

4. The method of claim 1, wherein $Q_2$ is a hydrogen atom or a lower alkyl group.

5. The method of claim 1, wherein X is an alkylene chain.

6. The method of claim 1, wherein both $R^1$ and $R^2$ are linear lower alkyls.

7. The method of claim 1, wherein $R^1$ and $R^2$ bind together to form —Z—(Z represents a carbon chain having a chain length of 2 to 4 atoms as the linear moiety which may have one or more side chains).

8. The method of claim 1 for use to treat or prevent osteoporosis.

* * * * *